United States Patent [19]
Fujita et al.

[11] Patent Number: 5,635,108
[45] Date of Patent: Jun. 3, 1997

[54] LIQUID CRYSTALLINE COMPOUND HAVING CONJUGATED CARBON CHAIN AND LIQUID CRYSTAL COMPOSITION CONTAINING

[75] Inventors: Atsuko Fujita; Shuichi Matsui; Kazutoshi Miyazawa, all of Chiba, Japan

[73] Assignee: Chisso Corporation, Osaka-fu, Japan

[21] Appl. No.: 620,159

[22] Filed: Mar. 22, 1996

[30] Foreign Application Priority Data

Mar. 23, 1995 [JP] Japan ................................. 7-090277

[51] Int. Cl.$^6$ .................. C09K 19/30; C09K 19/52; G02F 1/13; C07C 43/02
[52] U.S. Cl. .................. 252/299.63; 252/299.01; 252/299.61; 252/299.64; 252/299.65; 252/299.66; 568/658; 349/182
[58] Field of Search .................. 252/299.01, 299.66, 252/299.61, 299.63; 359/103; 568/658

[56] References Cited

U.S. PATENT DOCUMENTS 5,068,053 11/1991 Reiffenrath et al. ............... 252/299.01
5,370,819 12/1994 Fujita et al. ............... 252/299.01

Primary Examiner—Shean C. Wu
Attorney, Agent, or Firm—Wenderoth, Lind & Ponack

[57] ABSTRACT

A hexynediene derivative expressed by the following general formula I and liquid crystal compositions containing the derivative are disclosed:

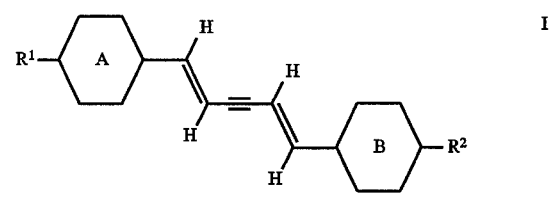

wherein $R^1$ and $R^2$ independently represent an alkyl group or alkoxy group each having 1 to 10 carbon atoms, ring A and ring B independently represent 1,4-cyclohexylene or 1,4-phenylene.

15 Claims, No Drawings

LIQUID CRYSTALLINE COMPOUND HAVING CONJUGATED CARBON CHAIN AND LIQUID CRYSTAL COMPOSITION CONTAINING

FIELD OF INVENTION

The present invention relates to a compound useful as a material for a liquid crystal. More specifically, the present invention relates to a liquid crystalline compound having a conjugated carbon chain in the molecule and a liquid crystal composition containing the compound.

BACKGROUND TECHNOLOGY

Display devices which employ a liquid crystal are widely used for watches, tabletop calculators, and others. These liquid crystal display devices employ optical anisotropy and dielectic anisotropy of a liquid crystal substance. Liquid crystal phase includes a nematic liquid crystal phase, smectic liquid crystal phase, and cholesteric liquid crystal phase. Devices which use a nematic liquid crystal phase are most widely put in practical use. Further, the mode used in liquid crystal display can be classified into TN (twisted nematic) type, DS (dynamic scattering) type, guest-host type, and DAP type from the aspect of electro-optic effect.

Heretofore, a large number of liquid crystalline compounds including those at a research stage are widely known. At present, however, no compound has been found which is enclosed and used in a display device as a single liquid crystal compound. This is because whereas a liquid crystalline compound which is expected as a material for a display device is desired to exhibit a liquid crystal phase at a temperature range as wide as possible, centered at a particular temperature at which the liquid crystal substance is most frequently used, and whereas the liquid crystal substance must be sufficiently stable against environmental factors to be used and must have physical properties sufficient to drive display devices, no substance which satisfies these requirements as a single compound has been found.

Then, several kinds of liquid crystalline compounds, that is, liquid crystal compound and non-liquid crystalline compounds are mixed to prepare compositions having such properties, and put in practical use as raw materials at present. These liquid crystal compositions are required to be stable even against moisture, light, heat, and air which usually exist under environment under which the compositions are used, and also they are required to be stable against electric field and electromagnetic radiation. Further, liquid crystalline compounds to be mixed are required to be stable each other under environment to be used. Besides, liquid crystal compositions are required to have appropriate values of such several physical properties as optical anisotropy, dielectric anisotropy, and electric conductivity depending on the modes of display and shape of devices. Particularly, the compositions are required such that the product of a value of their optical anisotropy (Δn) and thickness of a cell (d) show a constant value. Since a tendency for (d) mentioned above to reduce is increased to obtain good quality of displays having no domains in recent display devices, it has become important to increase the Δn of the compositions, and thus the need for a single liquid crystalline compound having a high Δn has become significant.

Heretofore, for examples, tolan derivatives expressed by the formula (a) below (Unexamined Japanese Patent Publication No. Hyo Hei 01-502823) or butadiyne derivatives expressed by the formula (b) below (Mol. Cryst. Liq. Cryst. 48, 175 (1978) are known in public. However, they have such defects that the former are narrow in their mesomorphic range and the latter are thermally instable. Thus neither material can be said to be sufficient to achieve the objects mentioned above.

Further, known stilbene derivatives expressed by the following formula (c) (Flussige Kristalle in Tabellen. Leipzig. VEB Deutsher Verlaugfur Grundstoffindustrie 1975, 49) and difluorostilbene derivatives expressed by the following formula (d) (Unexamined Japanese Patent Publication No. Hei 03-294386) which were recently developed with a purpose of stabilizing the stilbene derivatives are useful as raw materials for liquid crystal having a comparatively high Δn and a low viscosity. However, since neither material has a sufficiently wide mesomorphic range, they had no choice but to mix with other raw materials for liquid crystal having a high clearing point to compensate for the defects.

The present inventors have developed compounds having a conjugated eneyne structure as expressed by the following formula (e) with an object to develop new compounds which offset the defects of those materials mentioned above (Unexamined Japanese Patent Publication No. Hei 06-312946). However, even those compounds can hardly be said to have a sufficiently large Δn.

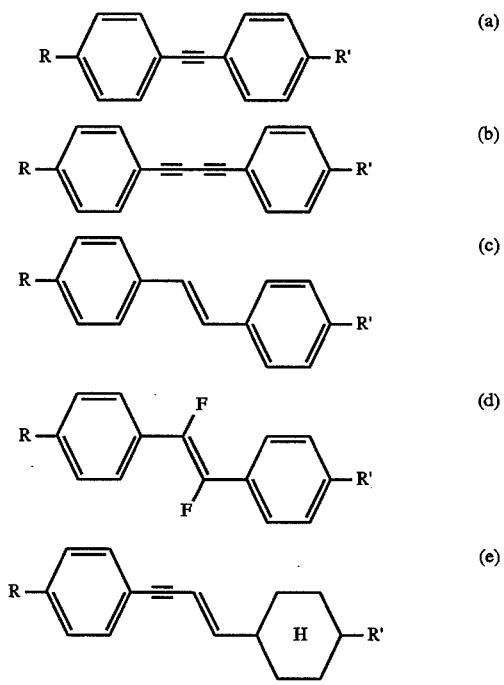

DISCLOSURE OF THE INVENTION

An object of the present invention is to solve the various problems mentioned above. Another object of the present invention is to provide a liquid crystalline compound which has an extremely large Δn, exhibits a wide mesomorphic range, has a good compatibility with other materials for liquid crystal, having a low viscosity, and shows a high reliability. Another object of the present invention is to provide a liquid crystal composition containing the liquid crystalline compound.

The present invention, which achieves the objects mentioned above and is claimed by the present application, is summarized as follows:

(1) A hexynediene derivative expressed by the following general formula I

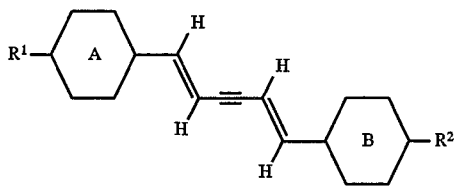

I wherein $R^1$ and $R^2$ independently represent an alkyl group or alkoxy group each having 1 to 10 carbon atoms, ring A and ring B independently represent 1,4-cyclohexylene or 1,4-phenylene.

(2) The hexynediene derivative recited in (1) wherein the ring A is 1,4-phenylene.

(3) The hexynediene derivative recited in (1) wherein the ring A is 1,4-cyclohexylene.

(4) The hexynediene derivative recited in (3) wherein the ring B is 1,4-phenylene.

(5) The hexynediene derivative recited in (3) wherein the ring B is 1,4-cyclohexylene.

(6) The hexynediene derivative recited in (5) wherein both $R^1$ and $R^2$ are an alkyl group having 1 to 10 carbon atoms, respectively.

(7) The hexynediene derivative recited in (5) wherein $R^1$ is an alkoxy group having 1 to 10 carbon atoms and $R^2$ is an alkyl group having 1 to 10 carbon atoms, respectively.

(8) A liquid crystal composition containing at least one liquid crystalline compound recited in any one of (1) to (7).

(9) A liquid crystal composition containing, as the first component, at least one compound recited in any one of (1) to (7), and containing, as the second component, at least one compound selected from the group consisting of the compounds expressed by the following general formula II, III, or IV

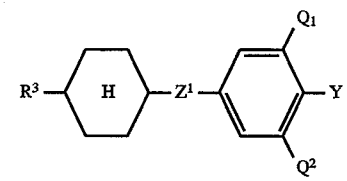

II

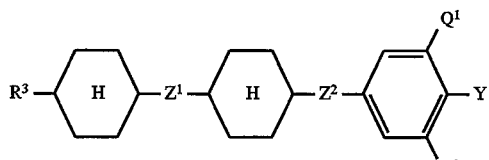

III

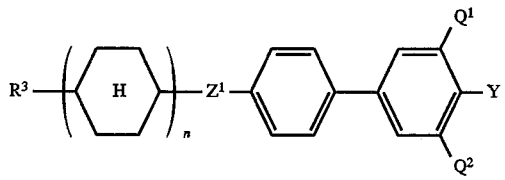

IV wherein $R^3$ represents an alkyl group having 1 to 10 carbon atoms, Y represents fluorine atom or chlorine atom, $Q^1$ and $Q^2$ independently represent hydrogen atom or fluorine atom, respectively, n represents 1 or 2, and $Z^1$ and $Z^2$ independently represent —$CH_2CH_2$— or a covalent bond.

(10) A liquid crystal composition containing, as the first component, at least one compound recited in any one of (1) to (7), and containing, as the second component, at least one compound selected from the group consisting of the compounds expressed by the following general formula V, VI, VII, VIII, or IX

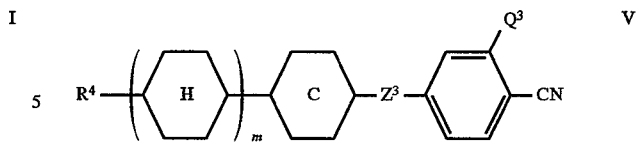

V

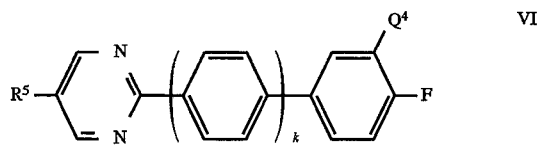

VI

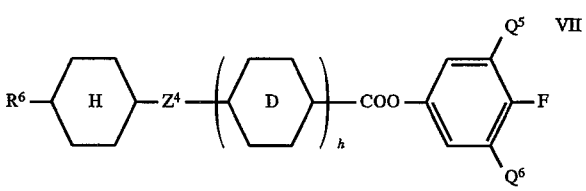

VII

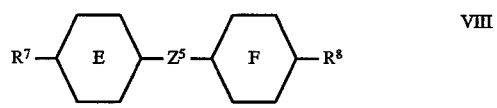

VIII

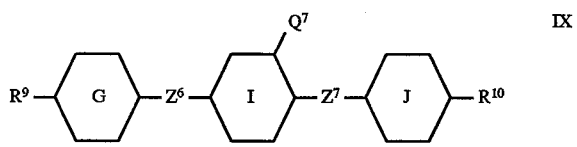

IX in the general formula V, $R^4$ represents an alkyl group having 1 to 10 carbon atoms or an alkenyl group having 2 to 10 carbon atoms, in either case, any methylene group (—$CH_2$—) may be replaced by an oxygen atom (—O—), but in neither case may two or more consecutive methylene groups be replaced by oxygen atoms $Z^3$ represents —$CH_2CH_2$—, —COO—, or a covalent bond; $Q^3$ represents a hydrogen atom or fluorine atom; ring C represents 1,4-cyclohexylene, 1,4-phenylene, or 1,3-dioxane-2,5-diyl, and m represents 0 or 1;

in the general formula VI, $R^5$ represents an alkyl group having 1 to 10 carbon atoms; $Q^4$ represents a hydrogen atom or fluorine atom; and k represents 0 or 1;

in the general formula VII, $R^6$ represents an alkyl group having 1 to 10 carbon atoms; ring D represents 1,4-cyclohexylene or 1,4-phenylene; $Q^5$ and $Q^6$ independently represent a hydrogen atom or fluorine atom, respectively; $Z^4$ represents —COO— or a covalent bond; and h represents 0 or 1;

in the general formula VIII, $R^7$ and $R^8$ independently represent an alkyl group having 1 to 10 carbon atoms or an alkenyl group having 2 to 10 carbon atoms, in either case, any methylene group (—$CH_2$—) may be replaced by an oxygen atom, but in no case may two or more consecutively methylene groups be replaced by oxygen atoms; ring E represents 1,4-cyclohexylene, 1,3-pyrimidine-2,5-diyl, or 1,4-phenylene; ring F represents 1,4-cyclohexylene or 1,4-phenylene; and $Z^5$ represents —C≡C—, —COO—, —$CH_2CH_2$—, or a covalent bond; and in the general formula IX, $R^9$ represents an alkyl group or alkoxy group each having 1 to 10 carbon atoms; $R^{10}$ represents an alkyl group, alkoxy group, or alkoxymethyl group each having 1 to 10 carbon atoms; ring G represents 1,4-cyclohexylene or 1,3-pyrimidine-2,5-diyl; Ring I and Ring J independently represent 1,4-cyclohexylene or 1,4-phenylene, respectively; $Z^6$ represents —COO—, —$CH_2CH_2$—, or a covalent bond; $Z^7$ represents —C≡C—, —COO—, or a covalent bond; and $Q^7$ represents a hydrogen atom or fluorine atom.

(11) A liquid crystal composition containing, as the first component, at least one liquid crystalline compound recited in any one of (1) to (7), containing, as a part of the second component, at least one compound selected from the group consisting of the compounds expressed by the general formula II, III, or IV, and containing, as the other part of the second component, at least one compound selected from the group consisting of the compounds expressed by the general formula V, VI, VII, VIII, or IX.

(12) A liquid crystal display device composed by using a liquid crystal composition recited in any one of (8) to (11).

BEST MODE FOR CONDUCTING THE INVENTION

More specifically, the compounds of the present invention expressed by the general formula I include those expressed by the formulas from I-A to I-C below.

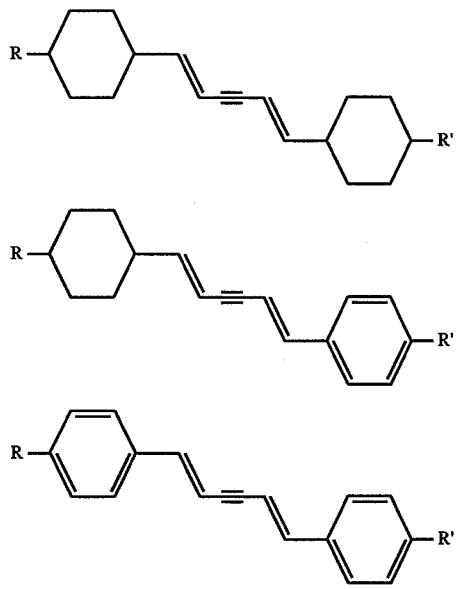

wherein R and R' independently represent an alkyl group or alkoxy group, respectively.

Among the compounds mentioned above, the compounds of the formula I-A are further divided into the formulas I-A1 and I-A2; so the compounds of the formula I-B to the formulas I-B1 and I-B2; and so the compounds of the formula I-C to the formulas IC1 and I-C2, respectively.

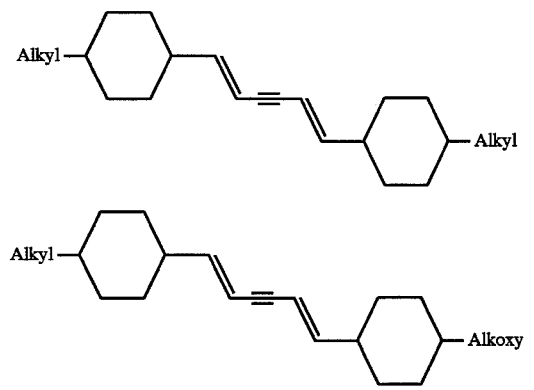

-continued

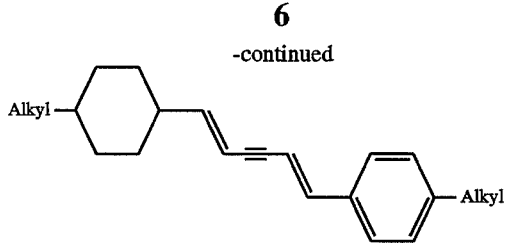

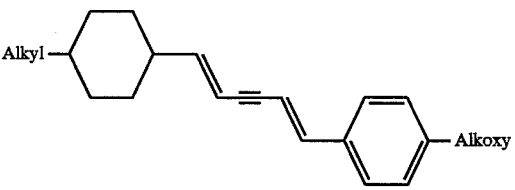

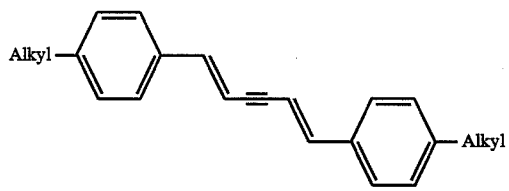

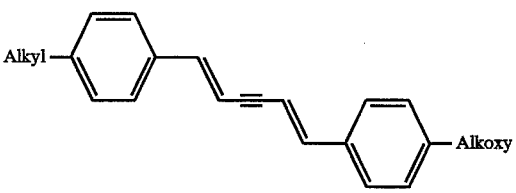

Any of these compounds of the present invention exhibits, as their characteristics, a large Δn, low viscosity, and wide mesomorphic range. That is, since the liquid crystalline compounds of the present invention have a highly conjugated middle carbon chain, even dicyclic compounds have such a wide mesomorphic range as comparable to that of tri- or tetracyclic compounds. Under the environment in which liquid crystal display devices are generally used, dicyclic compounds can be said to be most suitable.

Among them, the compounds which have two aromatic rings; are highly conjugated; and correspond to the formulas I-C1 and I-C2 are useful materials in the aspect that the compounds have an incomparably large Δn, in particular. The compounds which have an alkoxy group at the end of their molecule and correspond to the formulas I-A2, I-B2, or I-C2 have a wider mesomorphic range compared to the compounds in which the alkoxy group is replaced by an alkyl group, and the compounds have a slightly large Δn. Since the compounds corresponding to the formulas I-A1, I-A2, I-B1, or I-B2 have a cyclohexane ring, the compounds exhibit an improved light stability and thus they are useful. Further, the compounds which have an aromatic ring and a cyclohexane ring at the same time, and represented by the formula I-B1 or I-B2 exhibit comparably large Δn and wide mesomorphic range as well as an excellent compatibility, and thus they are useful. In this case, the alkyl groups or alkoxy groups at the ends of the molecule are preferably linear alkyl groups or alkoxy groups having 7 or less carbon atoms from the view point of expanding nematic mesomorphic range.

Since the compounds of the present invention have a hexynediene structure at the middle portion of the molecule, the compounds have 4 isomers derived from double bonds. Among them, the compounds in which both of the steric configuration of the double bonds are E isomeric can be used as more useful material for liquid crystal.

Liquid crystalline compounds of the present invention expressed by general formula I can easily be produced by a known general method of organic synthesis, for instance, by subjecting
an acetylene derivative expressed by the following formula

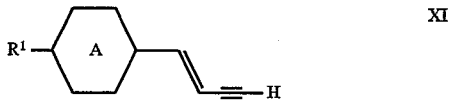

XI wherein ring A and $R^1$ have the same meaning as mentioned above, and
a derivative of a vinyl halide expressed by the following formula XII

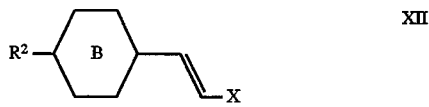

XII wherein X represents chlorine atom or bromine atom, ring B and $R^2$ have the same meaning as mentioned above,
to a coupling reaction in the presence of a catalyst of a transition metal complex and a promoter to be added when necessary, in an organic solvent.

The coupling reaction can be performed according to known procedures described, for instance, in Tetrahedron Letters Vol. 2, p 315 (1981).

As the complex catalyst, for example, palladium complexes of zerovalent or divalent such as dichlorobistriphenyl phosphine palladium, tetrakistriphenyl phosphine palladium, palladium acetate, and a Kharasch complex can be mentioned. The amount of the complex catalyst to be used is not identical since it depends on the reactivity of a substrate and other factors. However, it is suitably in the range of 0.1 to 20 mol %, and preferably, in particular, between 0.5 mol % and 5 mol %, since the period of time for conversion becomes short and side reactions become hard to occur.

As the promoter, a copper salt such as copper iodide and copper bromide is preferable from the aspect of increasing yield.

As the solvent to be used, diethylamine is generally most suitable. However, a polar solvent such as triethylamine, pyridine, morpholine, and dimethyl formamide, or a mixed solvent of one of these solvents with another suitable solvent can also be used.

As to the reaction temperature, it is sufficient to select it from the range of −40° C. to the boiling point of the solvent to be used. However, it is particularly preferable to select the temperature from the range of 0° C. to the boiling of the solvent, since catalyst activity can be maintained at a high level and conversion is high. Besides, the reaction mentioned above is preferably carried out in an inert gas since the active site of catalyst is instable against air and moisture.

When the compounds I of the present invention are separated after the termination of reaction, it is preferable to perform conventional after treatments, including particularly distillation for separating the complex catalyst remaining in the reaction system, and purification procedures such as a recrystallization and column chromatograph. Since the coupling reaction mentioned above proceeds while specifically maintaining the steric configuration of E isomer of a derivative of a vinyl halide XII which is one of the raw materials for the reaction, it is preferable to select a more useful E isomer or a mixture of the E isomer with a Z isomer, when the raw materials are used.

Among the compounds which are used as a raw material, an acetylene derivative XI can be obtained, for instance, by a method as shown below. That is, a vinyl halide expressed by the following formula XIII

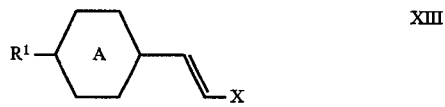

XIII wherein X represents chlorine atom or bromine atom, and ring A and $R^1$ have the same meaning as mentioned above,
and trimethylsilyl acetylene are subjected to a coupling reaction in a solvent to obtain a derivative of trimethylsilyl acetylene, and then to a separation of trimethylsilyl group from the derivative to obtain the acetylene derivative XI.

It is sufficient that the coupling reaction mentioned above and the succeeding steps until the resulting trimethylsilyl acetylene derivative is subjected to an after treatment are conducted under the conditions similar to those under which the liquid crystalline compounds are produced. That is, it is sufficient to conduct the reaction by using a similar catalyst, promoter, and solvent at a similar temperature, and to subject the product to similar after treatments.

Derivative of trimethylsilyl acetylene thus obtained can easily be converted into an acetylene derivative XI by treating the former derivative with potassium fluoride in a polar solvent or by treating the former derivative with potassium carbonate, potassium hydroxide, or sodium hydroxide in a solvent such as alcohol according to the method described in Preparative Acetylenic Chemistry, Second Edition, 1988.

Derivative of a vinyl halide XII (also, a derivative of a vinyl halide XIII) which is another raw material can easily be obtained by reacting a Wittig reaction agent which can be prepared from halogenated halomethyl triphenyl phosphonium readily available on the market with a corresponding aldehyde derivative according to the method described in Organic Reactions Vol. 14, 270 (1965).

Whereas the liquid crystal compositions provided by the present invention may comprise only the first component containing at least one liquid crystalline compound expressed by the general formula I, the compositions are preferably blended with, as the second component, at least one compound (hereinafter referred to as "second A component") selected from the group consisting of the compounds of the general formula II, III, or IV mentioned above and/or with at least one compound (hereinafter referred to as "second B component") selected from the group consisting of the compounds of the formulas V, VI, VII, VIII, and IX. Besides, it is possible to additionally blend, as the third component, a known compound with purposes of adjusting threshold voltage, mesomorphic range, Δn, dielectric anisotropy, and viscosity.

Among the second A components mentioned above, the following II-1 to II-12 can be mentioned as preferable examples of the compounds included in the general formula II; so the following III-1 to III-18 as preferable examples of the compounds included in general formula III; and so the following IV-1 to IV-18 as preferable examples of the compounds included in the general formula IV, respectively.

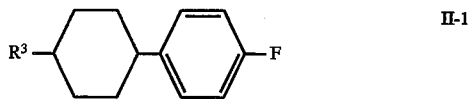

II-1

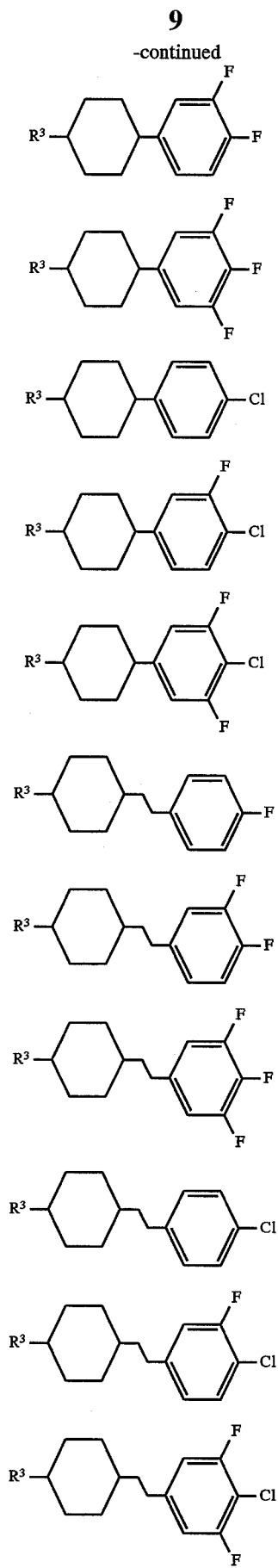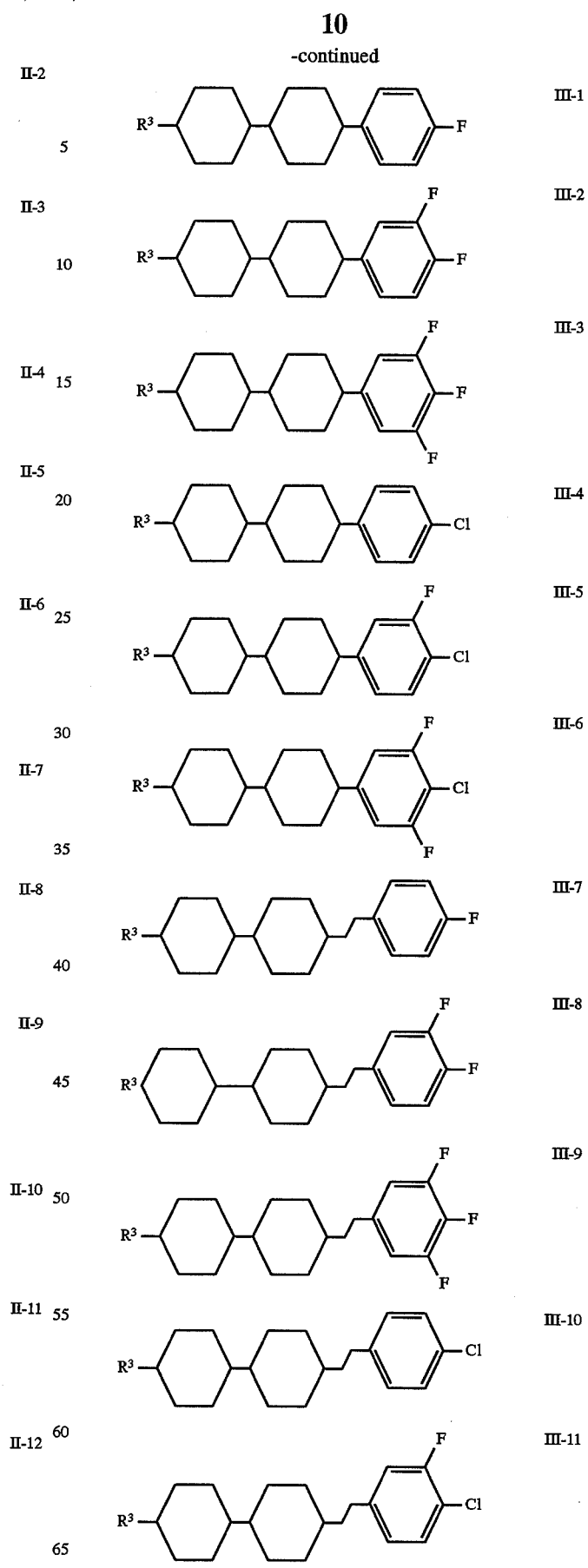

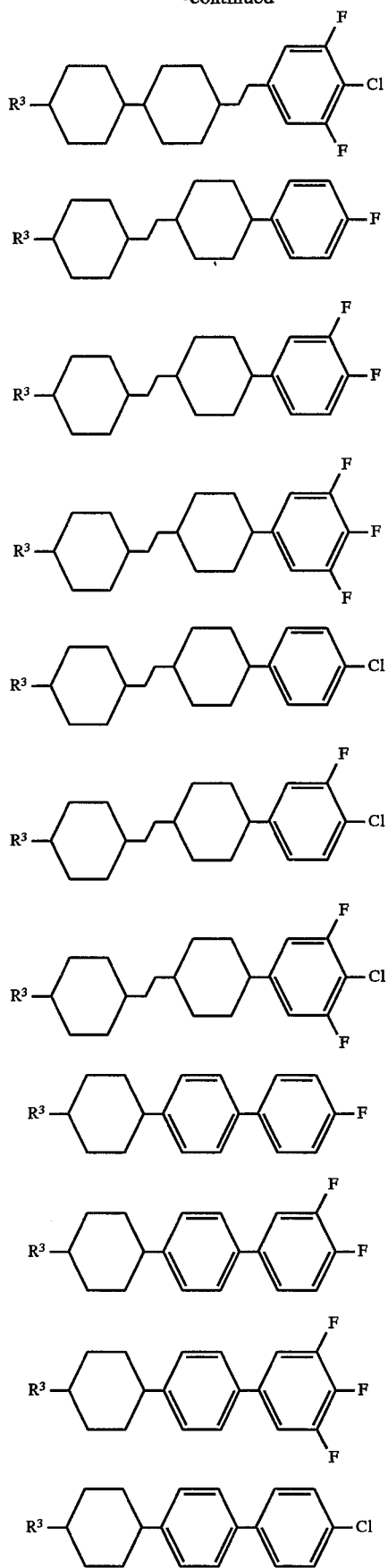

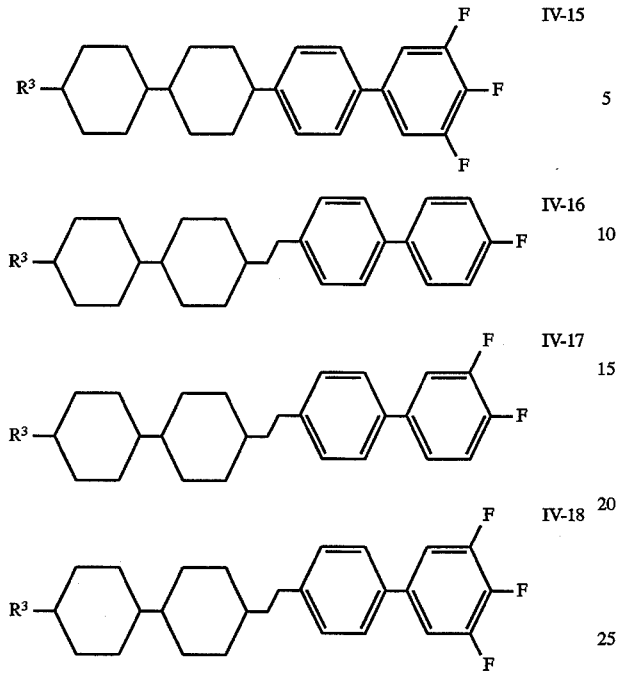

wherein R3 represents an alkyl group.

The compounds expressed by these general formulas II to IV have a positive dielectric anisotropy; are remarkably excellent in thermal stability and chemical stability; and are useful when a liquid crystal composition is prepared for TFT (AM-LCD) to which such a high reliability, that the voltage holding ratio is high or the value of specific resistance is large, is required, in particular.

Whereas the compounds may be used in an amount in any range based on the total weight of liquid crystal composition when liquid crystal compositions for TFT are prepared, the amount of the compounds to be used is preferably 10 to 97% by weight and more desirably 40 to 95% by weight.

Among the second B components mentioned above, V-1 to V-20, VI-1 to VI-3, and VII-1 to VII-11 can be mentioned as examples of the compounds included in the general formula V, VI or VII.

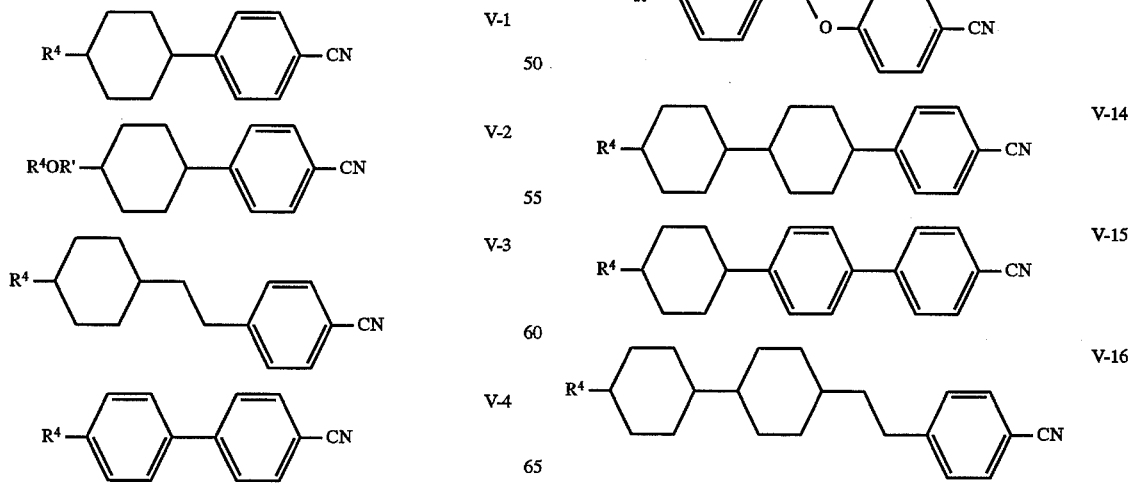

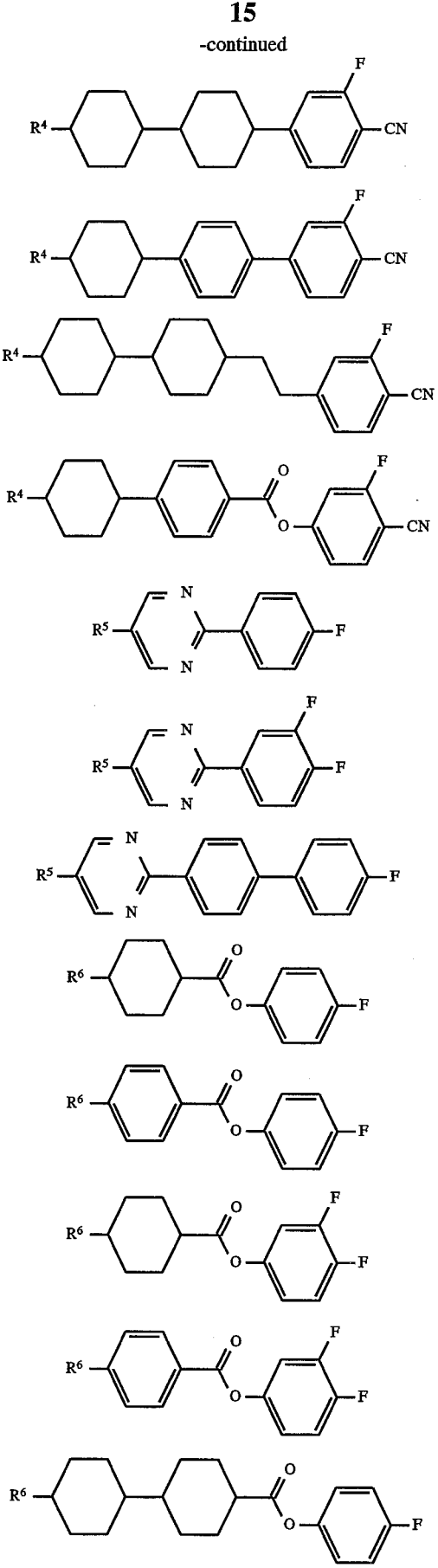

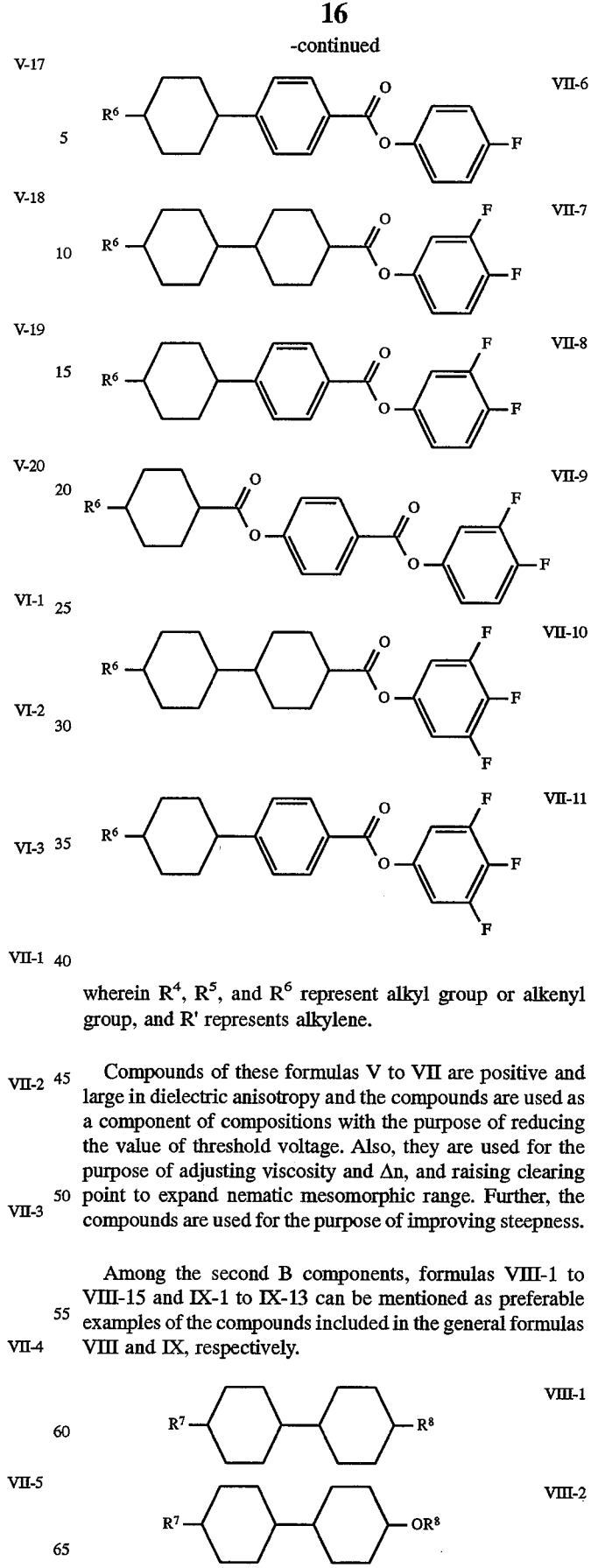

wherein $R^4$, $R^5$, and $R^6$ represent alkyl group or alkenyl group, and R' represents alkylene.

Compounds of these formulas V to VII are positive and large in dielectric anisotropy and the compounds are used as a component of compositions with the purpose of reducing the value of threshold voltage. Also, they are used for the purpose of adjusting viscosity and Δn, and raising clearing point to expand nematic mesomorphic range. Further, the compounds are used for the purpose of improving steepness.

Among the second B components, formulas VIII-1 to VIII-15 and IX-1 to IX-13 can be mentioned as preferable examples of the compounds included in the general formulas VIII and IX, respectively.

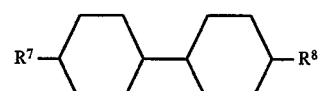

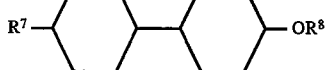

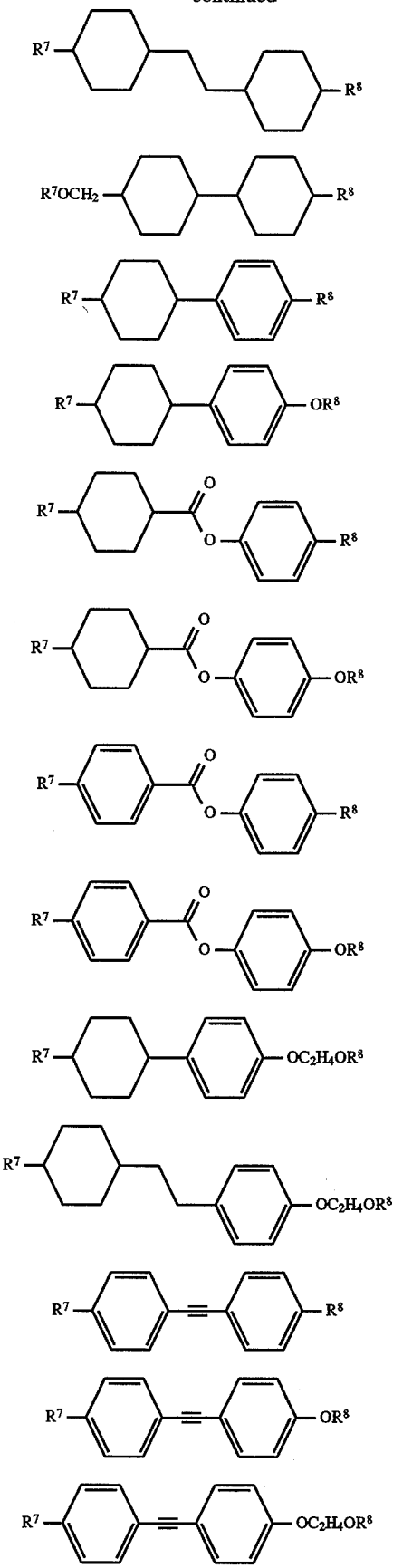
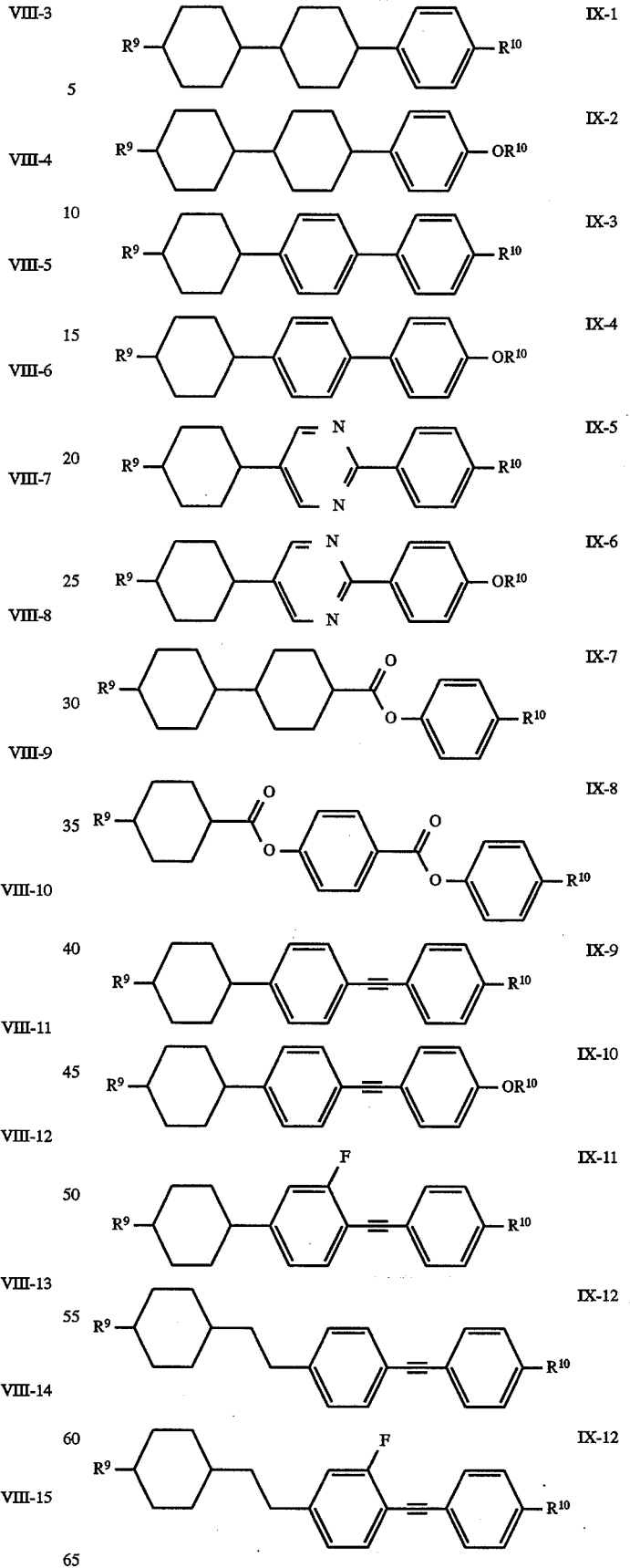
wherein $R^7$, $R^8$, $R^9$, and $R^{10}$ represent an alkyl group.

Compounds expressed by these formulas VIII and IX have a negative or small positive value of dielectric anisotropy. Among those compounds, the compounds of the formula VIII are mainly used with the purpose of lowering the viscosity and adjusting the Δn of the composition. The compounds of the formula IX are used with the purpose of, for instance, raising clearing point to widening nematic mesomorphic range of the composition and/or with the purpose of adjusting the Δn of the composition. Accordingly, the compounds of the formulas V through IX are useful particularly when liquid crystal compositions for STN display mode or TN display mode are prepared.

When the liquid crystal composition for TN display mode or STN display mode are prepared, the compounds can be used in an amount in any range adapted for the purpose. However, the amount of the compounds to be used is preferably 10 to 97% by weight and more desirably 40 to 95% by weight.

As mentioned above, the liquid crystal compositions for TFT may be composed of the first component and the second A component. However, the compositions may further contain the second B component as a part of the compositions. While liquid crystal compositions for STN or TN may be composed of the first component and the second B component, the compositions may contain the second A component as a part of the composition in addition to the former two components.

These liquid crystal compositions may further be admixed with the third component, and the following X-1 to X-33 can be mentioned as its preferable examples:

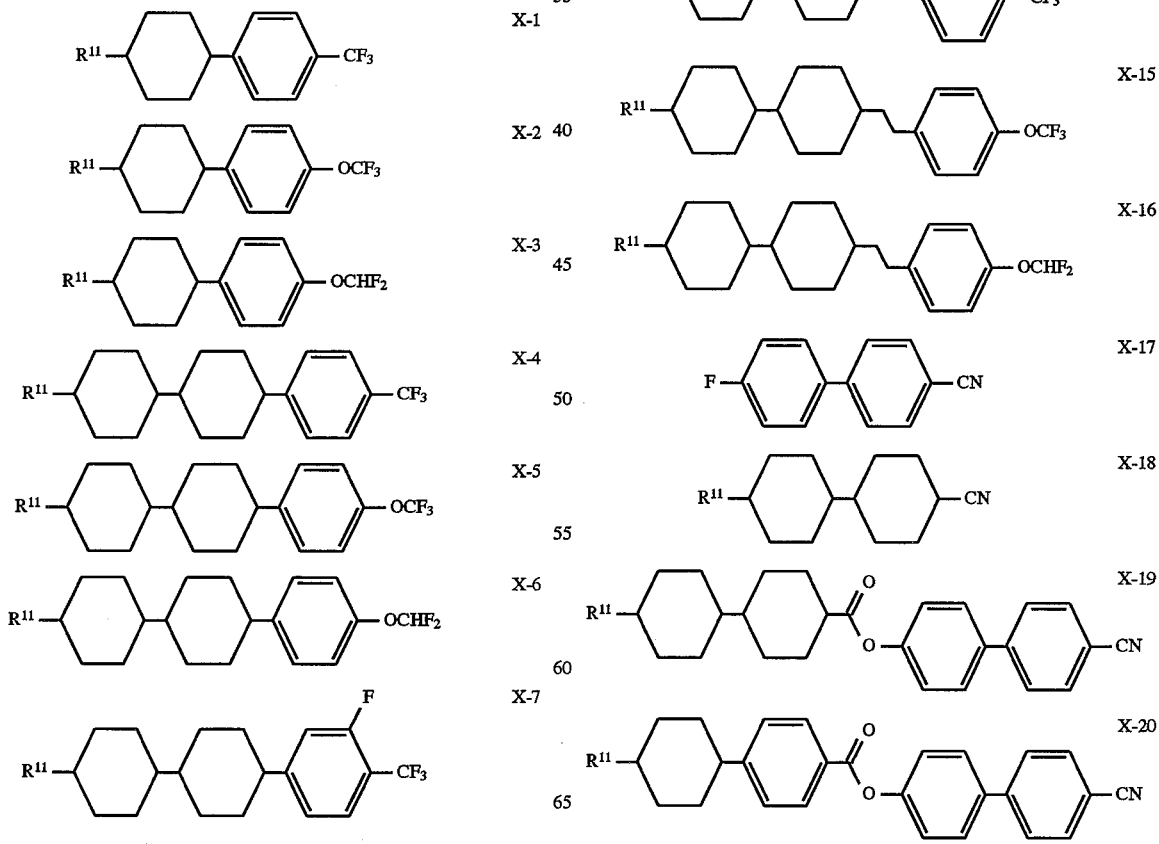

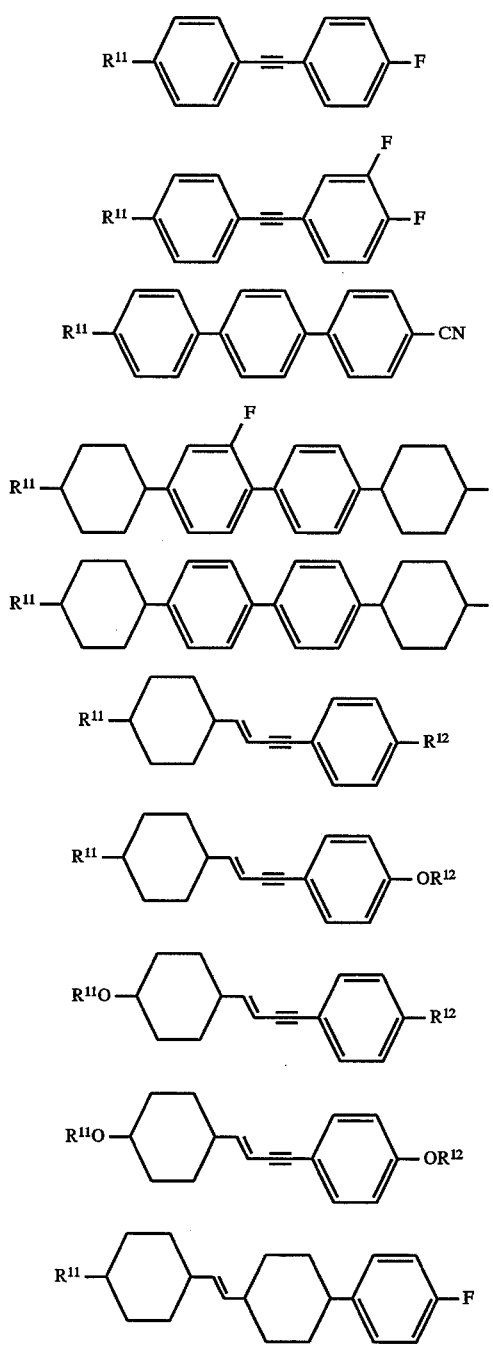
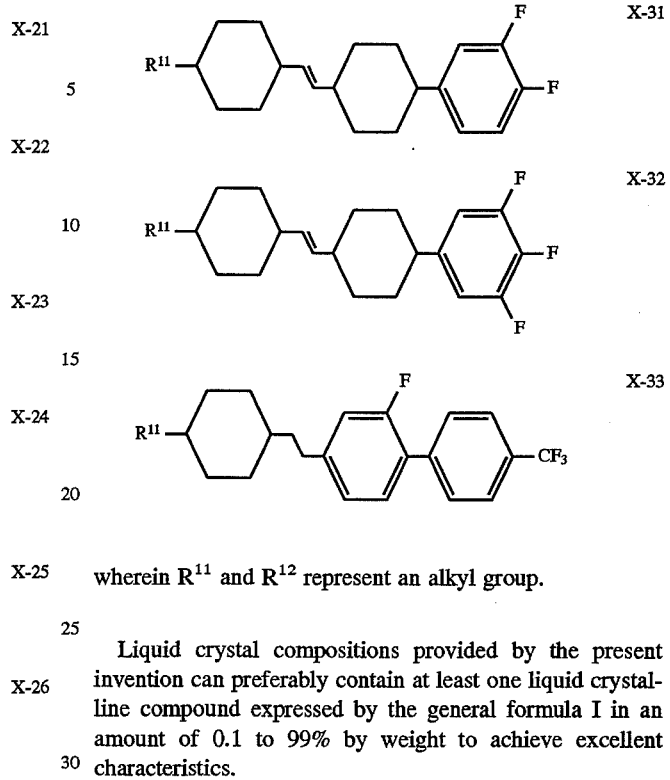

wherein $R^{11}$ and $R^{12}$ represent an alkyl group.

Liquid crystal compositions provided by the present invention can preferably contain at least one liquid crystalline compound expressed by the general formula I in an amount of 0.1 to 99% by weight to achieve excellent characteristics.

Liquid crystal compositions of the present invention can be further optimized by adding a proper additive depending on objective applications. As the additive, compounds are described in detail in literatures, for example, as chiral additives. The additives are added to induce the spiral structure of liquid crystal to adjust a required twist angle, and to prevent reverse twist. Liquid crystal compositions of the present invention which can be optimized by such a method as mentioned above can be prepared by a conventional method, for instance, by dissolving several liquid crystalline compounds to be contained each other at a temperature higher than an ambient temperature. Liquid crystal display devices having a wide operation temperature range and high speed response can be obtained by casting the liquid crystal composition thus prepared into a liquid crystal cell.

As the examples of liquid crystal compositions of the present invention, the following can be shown:

Composition Example 1

| | |
|---|---|
| 1,6-di(4-propylcyclohexyl)-1,5-hexadiene-3-yne | 5% by weight |
| 1-(trans-4-propylcyclohexyl)-6-(trans-4-ethylcyclohexyl)-1,5-hexadiene-3-yne | 5% by weight |
| 1-(trans-4-propylcyclohexyl)-6-(trans-4-pentylcyclohexyl)-1,5-hexadiene-3-yne | 4% by weight |
| 4-(trans-4-heptylcyclohexyl)-1,2-difluorobenzene | 2% by weight |
| 4-(2-(trans-4-pentylcyclohexyl)ethyl-1,2-difluorobenzene | 2% by weight |
| 4-(trans-4-propylcyclohexyl)ethoxybenzene | 3% by weight |
| 4-(trans-4-(trans-4-ethylcyclohexyl)cyclohexyl)-1,2-difluorobenzene | 13% by weight |

| | |
|---|---|
| 4-(trans-4-(trans-4-propylcyclohexyl)cyclohexyl)-1,2-difluorobenzene | 13% by weight |
| 4-(trans-4-(trans-4-pentylcyclohexyl)cyclohexyl)-1,2-difluorobenzene | 13% by weight |
| 4-(trans-4-(2-(trans-4-ethylcyclohexyl)ethyl)cyclohexyl)-1,2-difluorobenzene | 6% by weight |
| 4-(trans-4-(2-(trans-4-propylcyclohexyl)ethyl)cyclohexyl)-1,2-difluorobenzene | 3% by weight |
| 4-(trans-4-(2-(trans-4-pentylcyclohexyl)ethyl)cyclohexyl)-1,2-difluorobenzene | 6% by weight |
| 4'-(trans-4-ethlycyclohexyl)-3,4-difluorobiphenyl | 3% by weight |
| 4'-(trans-4-propylcyclohexyl)-3,4-difluorobiphenyl | 3% by weight |
| 4'-(trans-4-pentylcyclohexyl)-3,4-difluorobiphenyl | 6% by weight |
| 4'-(trans-4-ethylcyclohexyl)-4-fluorobiphenyl | 3% by weight |
| 4'-(trans-4-propylcyclohexyl)-4-fluorobiphenyl | 2% by weight |
| 4-(trans-4-(trans-4-propylcyclohexyl)cyclohexyl)benzene | 3% by weight |
| 4-fluorophenyl trans-4-(trans-4-propylcyclohexyl)cyclohexanecarboxylate | 2% by weight |
| 4-(trans-4-(trans-4-propylcyclohexyl)cyclohexyl)toluene | 3% by weight |

Composition Example 2

| | |
|---|---|
| 1-(4-pentylphenyl)-6-(trans-4-butylcyclohexyl)-1,5-hexadiene-3-yne | 5% by weight |
| 1-(trans-4-propylcyclohexyl)-6-(trans-4-ethoxycyclohexyl)-1-5-hexadiene-3-yne | 10% by weight |
| 1-(trans-4-propylcyclohexyl)-6-(trans-4-methoxycyclohexyl)-1,5-hexadiene-3-yne | 10% by weight |
| 5-(trans-4-heptylcyclohexyl)-1,2,3-trifluorobenzene | 4% by weight |
| 5-(trans-4-(trans-4-propylcyclohexyl)cyclohexyl)-1,2,3-trifluorobenzene | 7% by weight |
| 5-(trans-4-(2-(trans-4-propylcyclohexyl)ethyl)cyclohexyl)-1,2,3-trifluorobenzene | 3% by weight |
| 5-(2-(trans-4-(trans-4-propylcyclohexyl)cyclohexyl)ethyl-1,2,3-trifluorobenzene | 2% by weight |
| 4'-(trans-4-propylcyclohexyl)-3,4,5-trifluorobiphenyl | 13% by weight |
| 4'-(trans-4-pentylcyclohexyl)-3,4,5-trifluorobiphenyl | 10% by weight |
| 4'-(2-(trans-4-propylcyclohexyl)ethyl)-3,4,5-trifluorobiphenyl | 5% by weight |
| 4'-(2-(trans-4-butylcyclohexyl)ethyl)-3,4,5-trifluorobiphenyl | 5% by weight |
| 4'-(2-(trans-4-pentylcyclohexyl)ethyl)-3,4,5-trifluorobiphenyl | 5% by weight |
| 3,4,5-trifluorophenyl 4-(trans-4-propylcyclohexyl)benzoate | 2% by weight |
| 3,4,5-trifluorophenyl 4-(trans-4-butylcyclohexyl)benzoate | 2% by weight |
| 3,4,5-trifluorophenyl trans-4-(trans-4-propylcyclohexyl)cyclohexanecarboxylate | 8% by weight |
| 3,4,5-trifluorophenyl trans-4-(trans-4-butylcyclohexyl)cyclohexanecarboxylate | 5% by weight |
| 3,4,5-trifluorophenyl trans-4-(trans-4-pentylcyclohexyl)cyclohexanecarboxylate | 2% by weight |
| 4'-(trans-4-(trans-4-propylcyclohexyl)cyclohexyl)-3,4,5-trifluorobiphenyl | 2% by weight |

Composition Example 3

| | |
|---|---|
| 1-(4-propylphenyl)-6-(trans-4-propylcyclohexyl)-1,5-hexadiene-3-yne | 8% by weight |
| 1-(4-propylphenyl)-6-(trans-4-pentylcyclohexyl)-1,5-hexadiene-3-yne | 6% by weight |
| 1-(4-ethylphenyl)-6-(4-pentylphenyl)-1,5-hexadiene-3-yne | 4% by weight |
| 1-(4-pentylphenyl)-6-(4-butylphenyl)-1,5-hexadiene-3-yne | 4% by weight |
| 4-(trans-4-propylcyclohexyl)chlorobenzene | 4% by weight |
| 5-(trans-4-heptylcyclohexyl)-1,2,3-trifluorobenzene | 6% by weight |
| 4-fluorophenyl trans-4-propylcyclohexanecarboxylate | 2% by weight |
| 4'-(trans-4-ethylcyclohexyl)-3,4,5-trifluorobiphenyl | 7% by weight |
| 4'-(trans-4-propylcyclohexyl)-3,4,5-trifluorobiphenyl | 7% by weight |
| 4'-(trans-4-pentylcyclohexyl)-3,4,5-trifluorobiphenyl | 14% by weight |
| 4-(trans-4-(trans-4-ethylcyclohexyl)cyclohexyl)chlorobenzene | 4% by weight |
| 4-(trans-4-(trans-4-butylcyclohexyl)cyclohexyl)chlorobenzene | 8% by weight |
| 4-(trans-4-(trans-4-pentylcyclohexyl)cyclohexyl)chlorobenzene | 4% by weight |
| 4-(trans-4-(2-(trans-4-propylcyclohexyl)ethyl)cyclohexyl)-2-fluorochlorobenzene | 2% by weight |
| 4'-(trans-4-propylcyclohexyl)-3,4,5-trifluorobiphenyl | 8% by weight |
| 4'-(trans-4-pentylcyclohexyl)-3,4,5-trifluorobiphenyl | 7% by weight |
| 4'-ethyl-2-fluoro-4-(trans-4-propylcyclohexyl)stilbene | 3% by weight |
| 4'-fluoro-4-biphenyl=trans-4-(trans-4-propylcyclohexyl)cyclohexanecarboxylate | 2% by weight |

Composition Example 4

| | |
|---|---|
| 1,6-di(trans-4-propylcyclohexyl)-1,5-hexadiene-3-yne | 10% by weight |
| 1-(trans-4-propylcyclohexyl)-6-(trans-4-pentylcyclohexyl)-1,5-hexadiene-3-yne | 8% by weight |
| 1-(trans-4-propylcyclohexyl)-6-(trans-4-ethoxycyclohexyl)-1,5-hexadiene-3-yne | 5% by weight |

| | |
|---|---|
| 1-(4-propylphenyl)-6-(4-methylphenyl)-1,5-hexadiene-3-yne | 10% by weight |
| 4-(trans-4-(3-butenyl)cyclohexyl)benzonitrile | 8% by weight |
| 4-(trans-4-(3E-pentenyl)cyclohexyl)benzonitrile | 7% by weight |
| 4-(trans-4-propylcyclohexyl)benzonitrile | 15% by weight |
| 4-(trans-4-methoxymethylcyclohexyl)benzonitrile | 10% by weight |
| Trans-4-(trans-4-pentylcyclohexyl)butylcyclohexane | 3% by weight |
| Trans-4-(trans-4-pentylcyclohexyl)methoxymethylcyclohexane | 3% by weight |
| 4-(2-(4-ethylphenyl)ethynyl)anisole | 3% by weight |
| 4-(trans-4-(trans-4-ethylcyclohexyl)cyclohexyl)benzonitrile | 4% by weight |
| 4-(trans-4-(trans-4-propylcyclohexyl)cyclohexyl)benzonitrile | 4% by weight |
| 4-(trans-4-(trans-4-propylcyclohexyl)cyclohexyl)toluene | 5% by weight |
| 4-(trans-4-(trans-4-propylcyclohexyl)cyclohexyl)propylbenzene | 3% by weight |
| 4-ethyl-4'-(5-ethyl-1,3-pyrimidine-2-yl)biphenyl | 2% by weight |

Composition Example 5

| | |
|---|---|
| 1-(trans-4-ethylcyclohexyl)-6-(trans-4-propylcyclohexyl)-1,5-hexadiene-3-yne | 6% by weight |
| 1-(trans-4-propylcyclohexyl)-6-(trans-4-ethoxycyclohexyl)-1,5-hexadiene-3-yne | 8% by weight |
| 1-(trans-4-propylcyclohexyl)-6-(4-butoxycyclohexyl)-1,5-hexadiene-3-yne | 6% by weight |
| 4-(5-propyl-1,3-dioxane-2-yl)benzonitrile | 10% by weight |
| 4-(5-butyl-1,3-dioxane-2-yl)benzonitrile | 8% by weight |
| 4-cyanophenyl 4-ethylbenzoate | 10% by weight |
| 4-cyanophenyl 4-propylbenzoate | 6% by weight |
| 4-(5-propyl-1,3-pyrimidine-2-yl)-1,2-difluorobenzene | 8% by weight |
| 4-butoxyphenyl trans-4-propylcyclohexanecarboxylate | 8% by weight |
| 4-ethoxyphenyl trans-4-butylcyclohexanecarboxylate | 8% by weight |
| 4-ethoxyphenyl trans-4-propylcyclohexanecarboxylate | 8% by weight |
| 4-(trans-4-(trans-4-propylcyclohexyl)cyclohexyl)toluene | 5% by weight |
| 4'-cyano-4-biphenyl trans-4-(trans-4-propylcyclohexyl)cyclohexanecarboxylate | 3% by weight |
| 4'-cyano-4-biphenyl 4-(trans-4-propylcyclohexyl)benzoate | 3% by weight |
| 4'-cyano-4-biphenyl 4-(trans-4-pentylcyclohexyl)benzoate | 3% by weight |

Composition Example 6

| | |
|---|---|
| 1-(trans-4-pentylcyclohexyl)-6-(trans-4-propylcyclohexyl)-1,5-hexadiene-3-yne | 6% by weight |
| 1,6-di(trans-4-propylcyclohexyl)-1,5-hexadiene-3-yne | 5% by weight |
| 1-(4-propylphenyl)-6-(trans-4-pentylcyclohexyl)-1,5-hexadiene-3-yne | 6% by weight |
| 1-(4-(4-methoxyphenyl))-6-(4-ethylcyclohexyl)-1,5-hexadiene-3-yne | 5% by weight |
| 4-(trans-4-propylcyclohexyl)benzonitrile | 18% by weight |
| 4-(trans-4-propylcyclohexyl)-2-fluorobenzonitrile | 4% by weight |
| 4-(trans-4-propylcyclohexyl)ethoxybenzene | 2% by weight |
| 4-(5-pentyl-1,3-pyrimidine-2-yl)fluorobenzene | 8% by weight |
| 1-(4-methoxyphenyl)-2-(4-ethylphenyl)ethyne | 3% by weight |
| Trans-4-(trans-4-propylcyclohexyl)pentylcyclohexane | 5% by weight |
| Trans-4-(trans-4-butylcyclohexyl)propylcyclohexane | 5% by weight |
| 4-(trans-4-(trans-4-propylcyclohexyl)cyclohexyl)toluene | 8% by weight |
| 4-(trans-4-(trans-4-propylcyclohexyl)cyclohexyl)propylbenzene | 12% by weight |
| 4-(trans-4-(trans-4-propylcyclohexyl)cyclohexyl)methoxybenzene | 4% by weight |
| 4-(trans-4-(trans-4-propylcyclohexyl)cyclohexyl)benzonitrile | 3% by weight |
| 4-(trans-4-(trans-4-propylcyclohexyl)cyclohexyl)-2-fluorobenzonitrile | 2% by weight |
| 1-(4-ethylphenyl)-2-(4-(2-(trans-4-propylcyclohexyl)ethyl)phenyl)ethyne | 4% by weight |

Composition Example 7

| | |
|---|---|
| 1-(4-propylphenyl)-6-(4-ethoxyphenyl)-1,5-hexadiene-3-yne | 6% by weight |
| 1-(trans-4-propylcyclohexyl)-6-(4-ethoxyphenyl)-1,5-hexadiene-3-yne | 7% by weight |
| 1-(trans-4-propylcyclohexyl)-6-(4-methoxyphenyl)-1,5-hexadiene-3-yne | 7% by weight |
| 1-(trans-4-pentylcyclohexyl)-6-(trans-4-propylcyclohexyl)-1,5-hexadiene-3-yne | 6% by weight |
| 4-pentyl-4'-cyanobiphenyl | 5% by weight |
| 4-(trans-4-propylcyclohexyl)-2-fluorobenzonitrile | 2% by weight |
| 4-(trans-4-propylcyclohexyl)ethoxybenzene | 10% by weight |
| 4-(5-ethyl-1,3-pyrimidine-2-yl)ethylbenzene | 5% by weight |
| 4-(5-propyl-1,3-pyrimidine-2-yl)ethylbenzene | 5% by weight |
| 4-(5-butyl-1,3-pyrimidine-2-yl)ethylbenzene | 5% by weight |
| 4-(5-pentyloxy-1,3-pyrimidine-2-yl)ethylbenzene | 4% by weight |
| 4-(5-hexyloxy-1,3-pyrimidine-2-yl)ethylbenzene | 4% by weight |
| 4-(5-heptyloxy-1,3-pyrimidine-2-yl)ethylbenzene | 4% by weight |
| 4-(5-octyloxy-1,3-pyrimidine-2-yl)ethylbenzene | 4% by weight |
| 4-(trans-4-(trans-4-propylcyclohexyl)cyclohexyl)toluene | 4% by weight |
| 4-(trans-4-(trans-4-propylcyclohexyl)cyclohexyl)propylbenzene | 8% by weight |
| 4-(trans-4-(trans-4-propylcyclohexyl)cyclohexyl)methoxybenzene | 5% by weight |

| | |
|---|---|
| 4-(trans-4-(trans-4-ethylcyclohexyl)cyclohexyl)toluene | 3% by weight |
| 5-propyl 2-(4-(trans-4-ethylcyclohexyl)phenyl-1,3-pyrimidine | 2% by weight |
| 4-(trans-4-(trans-4-propylcyclohexyl)cyclohexyl)fluorobenzene | 2% by weight |
| 4-fluoro-4'-(5-propyl-1,3-pyrimidine-2-yl)biphenyl | 2% by weight |
| Composition Example 8 | |
| 1,6-di(trans-4-propylcyclohexyl)-1,5-hexadiene-3-yne | 7% by weight |
| 1-(trans-4-pentylcyclohexyl)-6-(trans-4-ethoxycyclohexyl)-1,5-hexadiene-3-yne | 6% by weight |
| 1-(trans-4-pentylcyclohexyl)-6-(4-ethylphenyl)-1,5-hexadiene-3-yne | 5% by weight |
| 3-fluoro-4-cyanophenyl 4-ethoxymethylbenzoate | 6% by weight |
| 3-fluoro-4-cyanophenyl 4-propoxymethylbenzoate | 10% by weight |
| 3-fluoro-4-cyanophenyl 4-pentoxymethylbenzoate | 4% by weight |
| 3-fluoro-4-cyanophenyl 4-(3E-pentenyl)benzoate | 13% by weight |
| 4-(trans-4-propylcyclohexyl)ethoxybenzene | 5% by weight |
| Trans-4-(trans-4-propylcyclohexyl)butylcyclohexane | 3% by weight |
| 4-fluorophenyl trans-4-(trans-4-propylcyclohexyl)cyclohexanecarboxylate | 5% by weight |
| 4-fluorophenyl trans-4-(trans-4-pentylcyclohexyl)cyclohexanecarboxylate | 5% by weight |
| 4-fluorophenyl trans-4-(trans-4-propylcyclohexyl)benzoate | 3% by weight |
| 4-(trans-4-(trans-4-propylcyclohexyl)cyclohexyl)fluorobenzene | 2% by weight |
| 4-fluoro-4'-(trans-4-propylcyclohexyl)biphenyl | 2% by weight |
| 4-(trans-4-(trans-4-propylcyclohexyl)cyclohexyl)toluene | 6% by weight |
| 4-(trans-4-(trans-4-propylcyclohexyl)cyclohexyl)propylbenzene | 5% by weight |
| 4-(trans-4-(trans-4-propylcyclohexyl)cyclohexyl)methoxybenzene | 3% by weight |
| 1-(4-ethylphenyl)-2-(4-(2-(trans-4-propylcyclohexyl)ethyl)phenyl)ethyne | 2% by weight |
| 1-(4-propylphenyl)-2-(4-(2-(trans-4-propylcyclohexyl)ethyl)phenyl)ethyne | 2% by weight |
| 4-fluorophenyl (4-(trans-4-propylcyclohexyl)carbonyloxyphenyl)benzoate | 2% by weight |
| 1-(4-ethylphenyl)-2-(4-(trans-4-propylcyclohexyl)-2-fluorophenyl)ethyne | 4% by weight |
| Composition Example 9 | |
| 1-(trans-4-propylcyclohexyl)-6-(trans-4-methoxycyclohexyl)-1,5-hexadiene-3-yne | 6% by weight |
| 1-(trans-4-propylcyclohexyl)-6-(4-propylphenyl)-1,5-hexadiene-3-yne | 5% by weight |
| 4-(trans-4-pentylcyclohexyl)fluorobenzene | 8% by weight |
| Trans-4-(trans-4-propylcyclohexyl)methoxycyclohexane | 3% by weight |
| Trans-4-(trans-4-propylcyclohexyl)propoxycyclohexane | 3% by weight |
| Trans-4-(trans-4-pentylcyclohexyl)ethoxycyclohexane | 3% by weight |
| 4-(trans-4-(trans-4-propylcyclohexyl)cyclohexyl)difluoromethoxybenzene | 8% by weight |
| 4-(trans-4-(trans-4-pentylcyclohexyl)cyclohexyl)difluoromethoxybenzene | 8% by weight |
| 5-(trans-4-(trans-4-propylcyclohexyl)cyclohexyl)-1,3-difluoro-2-difluoromethoxybenzene | 6% by weight |
| 5-(trans-4-(trans-4-pentylcyclohexyl)cyclohexyl)-1,3-difluoro-2-difluoromethoxybenzene | 6% by weight |
| 4-(trans-4-(trans-4-ethylcyclohexyl)cyclohexyl)trifluoromethoxybenzene | 12% by weight |
| 4-(trans-4-(trans-4-propylcyclohexyl)cyclohexyl)trifluoromethoxybenzene | 10% by weight |
| 4-(2-(trans-4-(trans-4-propylcyclohexyl)cyclohexyl)ethyl-1,2-difluorobenzene | 10% by weight |
| 4-(2-(trans-4-(trans-4-pentylcyclohexyl)cyclohexyl)ethyl-1,2-difluorobenzene | 6% by weight |
| 3,4-difluorophenyl (trans-4-(trans-4-propylcyclohexyl)cyclohexanecarboxylate | 6% by weight |
| Composition Example 10 | |
| 1-(trans-4-pentylcyclohexyl)-6-(4-propylphenyl)-1,5-hexadiene-3-yne | 7% by weight |
| 1-(trans-4-propylcyclohexyl)-6-(4-ethoxyphenyl)-1,5-hexadiene-3-yne | 7% by weight |
| 1-(4-ethylphenyl)-6-(4-propylphenyl)-1,5-hexadiene-3-yne | 4% by weight |
| 1-(4-pentylphenyl)-6-(4-methoxyphenyl)-1,5-hexadiene-3-yne | 3% by weight |
| 4-(trans-4-ethenylcyclohexyl)benzonitrile | 5% by weight |
| 3,4-difluorophenyl trans-4-butylcyclohexanecarboxylate | 8% by weight |
| 3,4-difluorophenyl trans-4-pentylcyclohexanecarboxylate | 5% by weight |
| 3-fluoro-4-cyanophenyl trans-4-ethylcyclohexanecarboxylate | 5% by weight |
| 3-fluoro-4-cyanophenyl trans-4-propylcyclohexanecarboxylate | 5% by weight |
| 3-fluoro-4-cyanophenyl trans-4-butylcyclohexanecarboxylate | 5% by weight |
| 3-fluoro-4-cyanophenyl trans-4-pentylcyclohexanecarboxylate | 5% by weight |
| 4-(trans-4-methoxypropylcyclohexyl)-2-fluorobenzonitrile | 6% by weight |
| 3,4-difluorophenyl trans-4-(trans-4-propylcyclohexyl) | 6% by weight |

| | |
|---|---|
| cyclohexanecarboxylate | |
| 3,4-difluorophenyl trans-4-(trans-4-pentylcyclohexyl) cyclohexanecarboxylate | 4% by weight |
| 3-fluoro-4-cyanophenyl 4-(trans-4-ethylcyclohexyl)benzoate | 4% by weight |
| 3-fluoro-4-cyanophenyl 4-(trans-4-propylcyclohexyl)benzoate | 4% by weight |
| 3-fluoro-4-cyanophenyl 4-(trans-4-butylcyclohexyl)benzoate | 4% by weight |
| 3-fluoro-4-cyanophenyl 4-(trans-4-pentylcyclohexyl)benzoate | 4% by weight |
| 1-(4-ethylphenyl)-2-(4-(trans-4-propylcyclohexyl)phenyl)ethyne | 3% by weight |
| Trans-4-(trans-4-(1E-butenyl)cyclohexyl)propylcyclohexane | 4% by weight |
| 4-(trans-4-(trans-4-(5-hexenyl)cyclohexyl)cyclohexyl)toluene | 2% by weight |

Compounds of the present invention have a conjugated carbon chain in the molecule, and thus the compounds exhibit a large Δn, and have a wide mesomorphic range and a low viscosity even when they are dicyclic compounds. Further, the compounds are sufficiently stable under the environment in which liquid crystal devices are used; do not cause deterioration even under the conditions of electromagnetic radiation and voltage application; are excellent in compatibility with other materials of liquid crystal when used as a component of liquid crystal composition; and thus can provide liquid crystal composition having useful characteristics.

The present invention will be explained in more detail below with reference to Examples. In Examples, C represents a crystal phase, $S_A$ a smectic A phase, $S_B$ a smectic B phase, N a nematic phase, I represents an isotropic liquid phase, respectively, and the unit of phase transition temperature is °C. in every Example.

EXAMPLE 1

Synthesis of 1,6-di(trans-4-propylcyclohexyl)-1,5-hexadiene-3-yne (Compound No. 1)

Chlorobistriphenylphosphine palladium (350 mg) and copper iodide (50 mg) were put in a flask, the atmosphere in the flask was purged by argon, then a diethylamine solution of 1-(trans-4-propylcyclohexyl)-2-bromoethylene (3.5 g) was added under the argon atmosphere, and a diethylamine solution of trimethylsilylacetylene (2.0 g) was further dropwise added while stirring at an ambient temperature. After completion of the addition, they were stirred for 5 hours more at an ambient temperature. After termination of the stirring, water was added to the reaction system and it was extracted with heptane. The organic layer was washed with water, dried over anhydrous magnesium sulfate, and then concentrated under a reduced pressure. Brown oily product thus obtained was purified with a silica gel short column, and then recrystallized from ethanol to obtain a colorless oily product (2.1 g). From the results of instrumental analyses, this product was confirmed to be 1-trimethylsilyl-4-(trans-4-propylcyclohexyl)-3-butene-1-yne.

This compound (2.1 g) and potassium hydroxide (0.6 g) were dissolved in methanol, and heated while stirring to react under reflux conditions for 2 hours. After termination of the reaction, the solution was added with water and then extracted with heptane. Organic layer thus obtained was washed with water, dried over anhydrous magnesium sulfate, and then concentrated under a reduced pressure to obtain yellow oily product. This product was purified by using a silica gel column chromatogram to obtain a colorless oily product. From the results of instrumental analyses, this product was confirmed to be 4-(trans-4-propylcyclohexyl)-3-butene-1-yne.

Chlorobistriphenylphosphine palladium (350 mg) and copper iodide (50 mg) were put in a flask, the atmosphere in the flask was purged by argon, and then a diethylamine solution of 1-(4-propylcyclohexyl)-2-bromoethylene (0.7 g) was added under the argon atmosphere. While stirring the solution at an ambient temperature, a diethylamine solution of the 4-(trans-4-propylcyclohexyl)-3-butene-1-yne mentioned above (0.7 g) was dropwise added. After completion of the addition, the solution was stirred at an ambient temperature for 5 hours more to react, and then water was added to the reaction system and they were extracted with heptane. Organic layer was washed with water, dried over anhydrous magnesium sulfate, and then concentrated under a reduced pressure. Brown oily product thus obtained was purified with a silica gel short column, and recrystallized from ethanol to obtain a colorless oily product (1.0 g). This product was confirmed to be the captioned compound from the results of instrumental analyses.

C 33.0 $S_B$ 92.6 $S_A$ 96.3 N 147.7 I

The following compounds were synthesized in the same method as in Example 1:
Compound No.

2. 1,6-di(trans-4-ethylcyclohexyl)-1,5-hexadiene-3-yne
3. 1-(trans-4-ethylcyclohexyl)-6-(trans-4-propylcyclohexyl)-1,5-hexadiene-3-yne
4. 1-(trans-4-ethylcyclohexyl)-6-(trans-4-butylcyclohexyl)-1,5-hexadiene-3-yne
5. 1-(trans-4-ethylcyclohexyl)-6-(trans-4-pentylcyclohexyl)-1,5-hexadiene-3-yne
6. 1-(trans-4-propylcyclohexyl)-6-(trans-4-butylcyclohexyl)-1,5-hexadiene-3-yne
7. 1-(trans-4-propylcyclohexyl)-6-(trans-4-pentylcyclohexy)-1,5-hexadiene-3-yne
8. 1-(trans-4-propylcyclohexyl)-6-(trans-4-hexylcyclohexyl)-1,5-hexadiene-3-yne
9. 1-(trans-4-propylcyclohexyl)-6-(trans-4-heptylcyclohexyl)-1,5-hexadiene-3-yne
10. 1,6-di(trans-4-butylcyclohexyl)-1,5-hexadiene-3-yne
11. 1-(trans-4-butylcyclohexyl)-6-(trans-4-pentylcyclohexyl)-1,5-hexadiene-3-yne
12. 1-(trans-4-butylcyclohexyl)-6-(trans-4-hexylcyclohexyl)-1,5-hexadiene-3-yne
13. 1-(trans-4-butylcyclohexyl)-6-(trans-4-heptylcyclohexyl)-1,5-hexadiene-3-yne
14. 1,6-di(trans-4-pentylcyclohexyl)-1,5-hexadiene-3-yne
15. 1-(trans-4-pentylcyclohexyl)-6-(trans-4-hexylcyclohexyl)-1,5-hexadiene-3-yne
16. 1-(trans-4-pentylcyclohexyl)-6-(trans-4-heptylcyclohexyl)-1,5-hexadiene-3-yne
17. 1,6-di(trans-4-hexylcyclohexyl)-1,5-hexadiene-3-yne
18. 1-(trans-4-hexylcyclohexyl)-6-(trans-4-heptylcyclohexyl)-1,5-hexadiene-3-yne
19. 1,6-di(trans-4-heptylcyclohexyl)-1,5-hexadiene-3-yne
20. 1-(trans-4-ethylcyclohexyl)-6-(trans-4-methoxycyclohexyl)-1,5-hexadiene-3-yne 21. 1-(trans-4-ethylcyclohexyl)-6-(trans-4-ethoxycyclohexyl)-1,5-hexadiene-3-yne
22. 1-(trans-4-ethylcyclohexyl)-6-(trans-4-propoxycyclohexyl)-1,5-hexadiene-3-yne
23. 1-(trans-4-ethylcyclohexyl)-6-(trans-4-butoxycyclohexyl)-1,5-hexadiene-3-yne
24. 1-(trans-4-propylcyclohexyl)-6-(trans-4-methoxycyclohexyl)-1,5-hexadiene-3-yne
25. 1-(trans-4-propylcyclohexyl)-6-(trans-4-ethoxycyclohexyl)-1,5-hexadiene-3-yne
26. 1-(trans-4-propylcyclohexyl)-6-(trans-4-propoxycyclohexyl)-1,5-hexadiene-3-yne
27. 1-(trans-4-propylcyclohexyl)-6-(trans-4-butoxycyclohexyl)-1,5-hexadiene-3-yne
28. 1-(trans-4-butylcyclohexyl)-6-(trans-4-methoxycyclohexyl)-1,5-hexadiene-3-yne
29. 1-(trans-4-butylcyclohexyl)-6-(trans-4-ethoxycyclohexyl)-1,5-hexadiene-3-yne
30. 1-(trans-4-butylcyclohexyl)-6-(trans-4-propoxycyclohexyl)-1,5-hexadiene-3-yne
31. 1-(trans-4-butylcyclohexyl)-6-(trans-4-butoxycyclohexyl)-1,5-hexadiene-3-yne
32. 1-(trans-4-butylcyclohexyl)-6-(trans-4-pentoxycyclohexyl)-1,5-hexadiene-3-yne
33. 1-(trans-4-pentylcyclohexyl)-6-(trans-4-methoxycyclohexyl)-1,5-hexadiene-3-yne
34. 1-(trans-4-pentylcyclohexyl)-6-(trans-4-ethoxycyclohexyl)-1,5-hexadiene-3-yne
35. 1-(trans-4-pentylcyclohexyl)-6-(trans-4-propoxycyclohexyl)-1,5-hexadiene-3-yne
36. 1-(trans-4-pentylcyclohexyl)-6-(trans-4-butoxycyclohexyl)-1,5-hexadiene-3-yne
37. 1-(trans-4-hexylcyclohexyl)-6-(trans-4-methoxycyclohexyl)-1,5-hexadiene-3-yne
38. 1-(trans-4-hexylcyclohexyl)-6-(trans-4-ethoxycyclohexyl)-1,5-hexadiene-3-yne
39. 1-(trans-4-hexylcyclohexyl)-6-(trans-4-propoxycyclohexyl)-1,5-hexadiene-3-yne
40. 1-(4-ethylphenyl)-6-(trans-4-ethylcyclohexyl)-1,5-hexadiene-3-yne
41. 1-(4-ethylphenyl)-6-(trans-4-propylcyclohexyl)-1,5-hexadiene-3-yne
42. 1-(4-ethylphenyl)-6-(trans-4-butylcyclohexyl)-1,5-hexadiene-3-yne
43. 1-(4-ethylphenyl)-6-(trans-4-pentylcyclohexyl)-1,5-hexadiene-3-yne
44. 1-(4-propylphenyl)-6-(trans-4-ethylcyclohexyl)-1,5-hexadiene-3-yne
45. 1-(4-propylphenyl)-6-(trans-4-propylcyclohexyl)-1,5-hexadiene-3-yne
46. 1-(4-propylphenyl)-6-(trans-4-butylcyclohexyl)-1,5-hexadiene-3-yne
47. 1-(4-propylphenyl)-6-(trans-4-pentylcyclohexyl)-1,5-hexadiene-3-yne
48. 1-(4-propylphenyl)-6-(trans-4-hexylcyclohexyl)-1,5-hexadiene-3-yne
49. 1-(4-propylphenyl)-6-(trans-4-heptylcyclohexyl)-1,5-hexadiene-3-yne
50. 1-(4-butylphenyl)-6-(trans-4-ethylcyclohexyl)-1,5-hexadiene-3-yne
51. 1-(4-butylphenyl)-6-(trans-4-propylcyclohexyl)-1,5-hexadiene-3-yne
52. 1-(4-butylphenyl)-6-(trans-4-bytylcyclohexyl)-1,5-hexadiene-3-yne
53. 1-(4-butylphenyl)-6-(trans-4-pentylcyclohexyl)-1,5-hexadiene-3-yne
54. 1-(4-butylphenyl)-6-(trans-4-hexylcyclohexyl)-1,5-hexadiene-3-yne
55. 1-(4-butylphenyl)-6-(trans-4-heptylcyclohexyl)-1,5-hexadiene-3-yne
56. 1-(4-pentylphenyl)-6-(trans-4-ethylcyclohexyl)-1,5-hexadiene-3-yne
57. 1-(4-pentylphenyl)-6-(trans-4-propylcyclohexyl)-1,5-hexadiene-3-yne
58. 1-(4-pentylphenyl)-6-(trans-4-butylcyclohexyl)-1,5-hexadiene-3-yne
59. 1-(4-pentylphenyl)-6-(trans-4-pentylcyclohexyl)-1,5-hexadiene-3-yne
60. 1-(4-pentylphenyl)-6-(trans-4-hexylcyclohexyl)-1,5-hexadiene-3-yne
61. 1-(4-pentylphenyl)-6-(trans-4-heptylcyclohexyl)-1,5-hexadiene-3-yne
62. 1-(trans-4-ethylcyclohexyl)-6-(4-methoxyphenyl)-1,5-hexadiene-3-yne
63. 1-(trans-4-ethylcyclohexyl)-6-(4-ethoxyphenyl)-1,5-hexadiene-3-yne
64. 1-(trans-4-ethylcyclohexyl)-6-(4-propoxyphenyl)-1,5-hexadiene-3-yne
65. 1-(trans-4-ethylcyclohexyl)-6-(4-butoxyphenyl)-1,5-hexadiene-3-yne
66. 1-(trans-4-propylcyclohexyl)-6-(4-methoxyphenyl)-1,5-hexadiene-3-yne
67. 1-(trans-4-propylcyclohexyl)-6-(4-ethoxyphenyl)-1,5-hexadiene-3-yne
68. 1-(trans-4-propylcyclohexyl)-6-(4-propoxyphenyl)-1,5-hexadiene-3-yne
69. 1-(trans-4-propylcyclohexyl)-6-(4-butoxyphenyl)-1,5-hexadiene-3-yne
70. 1-(trans-4-butylcyclohexyl)-6-(4-methoxyphenyl)-1,5-hexadiene-3-yne
71. 1-(trans-4-butylcyclohexyl)-6-(4-ethoxyphenyl)-1,5-hexadiene-3-yne
72. 1-(trans-4-butylcyclohexyl)-6-(4-propoxyphenyl)-1,5-hexadiene-3-yne
73. 1-(trans-4-butylcyclohexyl)-6-(4-butoxyphenyl)-1,5-hexadiene-3-yne
74. 1-(trans-4-butylcyclohexyl)-6-(4-pentoxyphenyl)-1,5-hexadiene-3-yne
75. 1-(trans-4-pentylcyclohexyl)-6-(4-methoxyphenyl)-1,5-hexadiene-3-yne
76. 1-(trans-4-pentylcyclohexyl)-6-(4-ethoxyphenyl)-1,5-hexadiene-3-yne
77. 1-(trans-4-pentylcyclohexyl)-6-(4-propoxyphenyl)-1,5-hexadiene-3-yne
78. 1-(trans-4-pentylcyclohexyl)-6-(4-butoxyphenyl)-1,5-hexadiene-3-yne
79. 1-(trans-4-hexylcyclohexyl)-6-(4-methoxyphenyl)-1,5-hexadiene-3-yne
80. 1-(trans-4-hexylcyclohexyl)-6-(4-ethoxyphenyl)-1,5-hexadiene-3-yne
81. 1-(trans-4-hexylcyclohexyl)-6-(4-propoxyphenyl)-1,5-hexadiene-3-yne
82. 1,6-di(phenylethylphenyl)-1,5-hexadiene-3-yne
83. 1-(4-ethylphenyl)-6-(4-propylphenyl)-1,5-hexadiene-3-yne
84. 1-(4-ethylphenyl)-6-(4-butylphenyl)-1,5-hexadiene-3-yne
85. 1-(4-ethylphenyl)-6-(4-pentylphenyl)-1,5-hexadiene-3-yne
86. 1-(4-propylphenyl)-6-(4-butylphenyl)-1,5-hexadiene-3-yne
87. 1-(4-propylphenyl)-6-(4-pentylphenyl)-1,5-hexadiene-3-yne
88. 1-(4-propylphenyl)-6-(4-hexylphenyl)-1,5-hexadiene-3-yne 89. 1-(4-propylphenyl)-6-(4-heptylphenyl)-1,5-hexadiene-3-yne 90. 1,6-di(4-butylphenyl)-1,5-hexadiene-3-yne 91. 1-(4-butylphenyl)-6-(4-pentylphenyl)-1,5-hexadiene-3-yne 92. 1-(4-butylphenyl)-6-(4-hexylphenyl)-1,5-hexadiene-3-yne 93. 1-(4-butylphenyl)-6-(4-heptylphenyl)-1,5-hexadiene-3-yne 94. 1,6-di(4-pentylphenyl)-1,5-hexadiene-3-yne 95. 1-(4-pentylphenyl)-6-(4-hexylphenyl)-1,5-hexadiene-3-yne 96. 1-(4-pentylphenyl)-6-(4-heptylphenyl)-1,5-hexadiene-3-yne 97. 1,6-di(4-hexylphenyl)-1,5-hexadiene-3-yne 98. 1-(4-hexylphenyl)-6-(4-heptylphenyl)-1,5-hexadiene-3-yne 99. 1,6-di(4-heptylphenyl)-1,5-hexadiene-3-yne 100. 1-(4-ethylphenyl)-6-(4-methoxyphenyl)-1,5-hexadiene-3-yne 101. 1-(4-ethylphenyl)-6-(4-ethoxyphenyl)-1,5-hexadiene-3-yne 102. 1-(4-ethylphenyl)-6-(4-propoxyphenyl)-1,5-hexadiene-3-yne 103. 1-(4-ethylphenyl)-6-(4-butoxyphenyl)-1,5-hexadiene-3-yne 104. 1-(4-propylphenyl)-6-(4-methoxyphenyl)-1,5-hexadiene-3-yne 105. 1-(4-propylphenyl)-6-(4-ethoxyphenyl)-1,5-hexadiene-3-yne 106. 1-(4-propylphenyl)-6-(4-propoxyphenyl)-1,5-hexadiene-3-yne 107. 1-(4-propylphenyl)-6-(4-butoxyphenyl)-1,5-hexadiene-3-yne 108. 1-(4-butylphenyl)-6-(4-methoxyphenyl)-1,5-hexadiene-3-yne 109. 1-(4-butylphenyl)-6-(4-ethoxyphenyl)-1,5-hexadiene-3-yne 110. 1-(4-butylphenyl)-6-(4-propoxyphenyl)-1,5-hexadiene-3-yne 111. 1-(4-butylphenyl)-6-(4-butoxyphenyl)-1,5-hexadiene-3-yne 112. 1-(4-butylphenyl)-6-(4-pentoxyphenyl)-1,5-hexadiene-3-yne 113. 1-(4-pentylphenyl)-6-(4-methoxyphenyl)-1,5-hexadiene-3-yne 114. 1-(4-pentylphenyl)-6-(4-ethoxyphenyl)-1,5-hexadiene-3-yne 115. 1-(4-pentylphenyl)-6-(4-propoxyphenyl)-1,5-hexadiene-3-yne 116. 1-(4-pentylphenyl)-6-(4-butoxyphenyl)-1,5-hexadiene-3-yne 117. 1-(4-hexylphenyl)-6-(4-methoxyphenyl)-1,5-hexadiene-3-yne 118. 1-(4-hexylphenyl)-6-(4-ethoxyphenyl)-1,5-hexadiene-3-yne 119. 1-(4-hexylphenyl)-6-(4-propoxyphenyl)-1,5-hexadiene-3-yne

EXAMPLE 2 (USE EXAMPLE 1)

Several physical properties of the liquid composition comprising the following compounds were determined:

1,6-di(trans-4-propylcyclohexyl)-1,5-hexadiene-3-yne

| (Compound No. 1) | 15% by weight |
|---|---|
| 4-(trans-4-propylcyclohexyl)benzonitrile | 20% by weight |
| 4-(trans-4-pentylcyclohexyl)benzonitrile | 31% by weight |
| 4-(trans-4-heptylcyclohexyl)benzonitrile | 21% by weight |
| 4-(trans-4-pentylcyclohexyl)-4'-cyanobiphenyl | 13% by weight |

Results were as follows:

| Clearing point: | 80.4° C. |
|---|---|
| Viscosity: | 27.8 m · Pa · sec. |
| Δn: | 0.1393 (30° C.) |

While the composition was left in a freezer at −20° C., precipitation of crystals was not observed even the passage of 40 days.

What is claimed is:

1. A hexynediene derivative expressed by the following general formula I

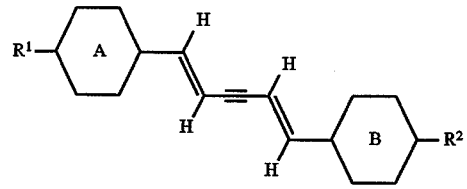

wherein $R^1$ and $R^2$ independently represent an alkyl group or alkoxy group each having 1 to 10 carbon atoms, ring A and ring B independently represent 1,4-cyclohexylene or 1,4-phenylene.

2. The hexynediene derivative according to claim 1 wherein the ring A is 1,4-phenylene.

3. The hexynediene derivative according to claim 1 wherein the ring A is 1,4-cyclohexylene.

4. The hexynediene derivative according to claim 3 wherein the ring B is 1,4-phenylene.

5. The hexynediene derivative according to claim 3 wherein the ring B is 1,4-cyclohexylene.

6. The hexynediene derivative according to claim 5 wherein both $R^1$ and $R^2$ are an alkyl group having 1 to 10 carbon atoms, respectively.

7. The hexynediene derivative according to claim 5 wherein $R^1$ is an alkoxy group having 1 to 10 carbon atoms and $R^2$ is an alkyl group having 1 to 10 carbon atoms, respectively.

8. A liquid crystal composition containing at least one liquid crystalline compound defined in any one of claims 1 to 7.

9. A liquid crystal composition containing, as the first component, at least one compound defined in any one of claims 1 to 7, and containing, as the second component, at least one compound selected from the group consisting of the compounds expressed by the following general formula II, III, or IV

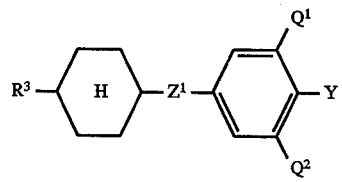

-continued

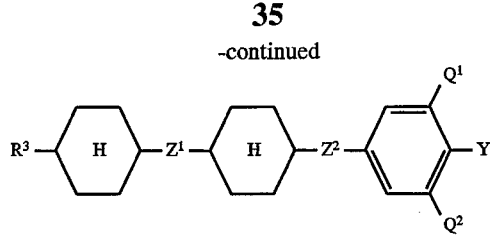  III

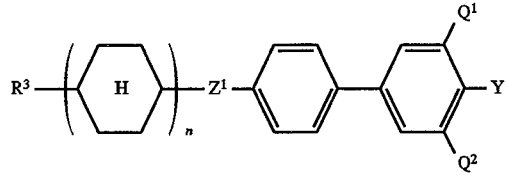  IV wherein R³ represents an alkyl group having 1 to 10 carbon atoms, Y represents fluorine atom or chlorine atom, Q¹ and Q² independently represent hydrogen atom or fluorine atom, respectively, n represents 1 or 2, and Z¹ and Z² independently represent —CH₂CH₂— or a covalent bond.

10. A liquid crystal display device composed by using a liquid crystal composition defined in claim 8.

11. A liquid crystal display device composed by using a liquid crystal composition defined in claim 9.

12. A liquid crystal composition containing, as the first component, at least one compound defined in any one of claims 1 to 7, and containing, as the second component, at least one compound selected from the group consisting of the compounds expressed by the general formula V, VI, VII, VIII, or IX

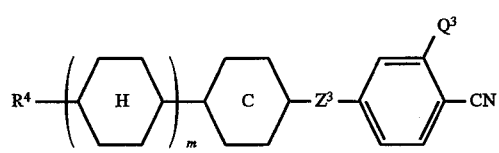  V

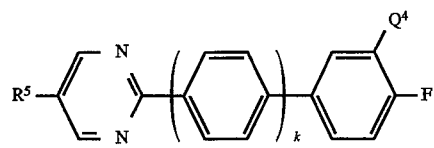  VI

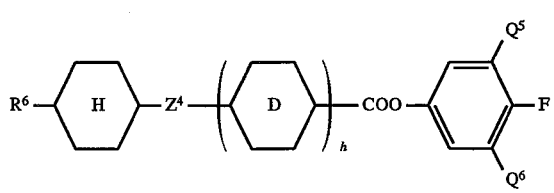  VII

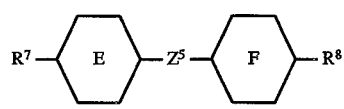  VIII

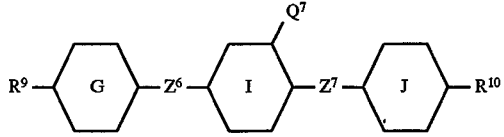  IX wherein in the general formula V, R⁴ represents an alkyl group having 1 to 10 carbon atoms or an alkenyl group having 2 to 10 carbon atoms, in either case, any methylene group (—CH₂—) may be replaced by an oxygen atom (—O—), but in neither case may two or more consecutive methylene groups be replaced by oxygen atoms; Z³ represents —CH₂CH₂—, —COO—, or a covalent bond; Q³ represents a hydrogen atom or fluorine atom; ring C represents 1,4-cyclohexylene, 1,4-phenylene, or 1,3-dioxane-2,5-diyl, and m represents 0 or 1;

in the general formula VI, R⁵ represents an alkyl group having 1 to 10 carbon atoms; Q⁴ represents a hydrogen atom or fluorine atom; and k represents 0 or 1;

in the general formula VII, R⁶ represents an alkyl group having 1 to 10 carbon atoms; ring D represents 1,4-cyclohexylene or 1,4-phenylene; Q⁵ and Q⁶ independently represent a hydrogen atom or fluorine atom, respectively; Z⁴ represents —COO— or a covalent bond; and h represents 0 or 1;

in the general formula VIII, R⁷ and R⁸ independently represent an alkyl group having 1 to 10 carbon atoms or an alkenyl group having 2 to 10 carbon atoms, in either case, any methylene group (—CH₂—) may be replaced by an oxygen atom, but in no case may two or more consecutive methylene groups be replaced by oxygen atoms; ring E represents 1,4-cyclohexylene, 1,3-pyrimidine-2,5-diyl, or 1,4-phenylene; ring F represents 1,4-cyclohexylene or 1,4-phenylene; and Z⁵ represents —C≡C—, —COO—, —CH₂CH₂—, or a covalent bond; and in the general formula IX, R⁹ represents an alkyl group or alkoxy group each having 1 to 10 carbon atoms; R¹⁰ represents an alkyl group, alkoxy group, or alkoxymethyl group each having 1 to 10 carbon atoms; ring G represents 1,4-cyclohexylene or 1,3-pyrimidine-2,5-diyl; ring I and ring J independently represent 1,4-cyclohexylene or 1,4-phenylene, respectively; Z⁶ represents —COO—, —CH₂CH₂—, or a covalent bond; Z⁷ represents —C≡C—, —COO—, or a covalent bond; and Q⁷ represents a hydrogen atom or fluorine atom.

13. A liquid crystal composition containing:

as the first component, at least one liquid crystalline compound defined in any one of claims 1 to 7, as a part of the second component, at least one compound selected from the group consisting of the compounds expressed by the general formula II, III or IV,

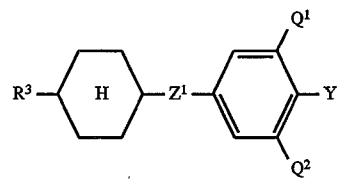  II

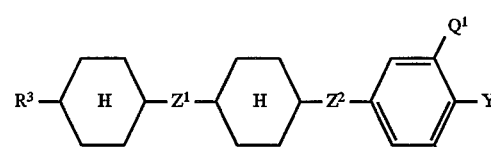  III

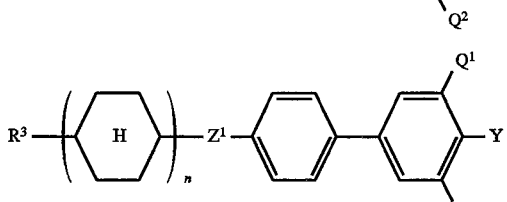  IV wherein R³ represents an alkyl group having 1 to 10 carbon atoms, Y represents fluorine atom or chlorine atom, Q¹ and Q² independently represent hydrogen atom or fluorine atom, respectively, n represents 1 or 2, and $Z^1$ and $Z^2$ independently represent —$CH_2CH_2$— or a covalent bond, and as the other part of the second component, at least one compound selected from the group consisting of the compounds expressed by the general formula V, VI, VII, VIII or IX,

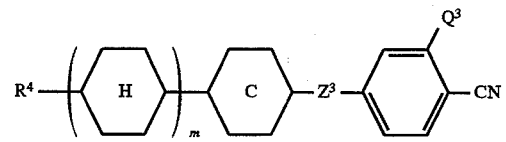
V

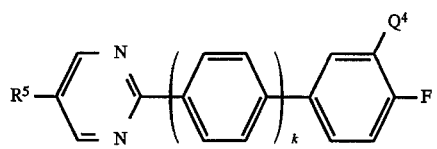
VI

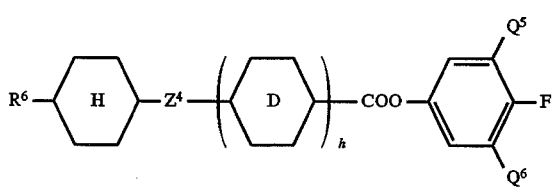
VII

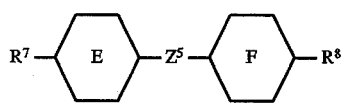
VIII

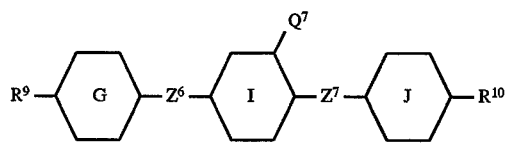
IX wherein in the general formula V, $R^4$ represents an alkyl group having 1 to 10 carbon atoms or an alkenyl group having 2 to 10 carbon atoms, in either case, any methylene group (—$CH_2$—) may be replaced by an oxygen atom (—O—), but in neither case may two or more consecutive methylene groups be replaced by oxygen atoms; $Z^3$ represents —$CH_2CH_2$—, —COO—, or a covalent bond; $Q^3$ represents a hydrogen atom or fluorine atom; ring C represents 1,4-cyclohexylene, 1,4-phenylene, or 1,3-dioxane-2,5-diyl, and m represents 0 or 1;

in the general formula VI, $R^5$ represents an alkyl group having 1 to 10 carbon atoms; $Q^4$ represents a hydrogen atom or fluorine atom; and k represents 0 or 1;

in the general formula VII, $R^6$ represents an alkyl group having 1 to 10 carbon atoms; ring D represents 1,4-cyclohexylene or 1,4-phenylene; $Q^5$ and $Q^6$ independently represent a hydrogen atom or fluorine atom, respectively; $Z^4$ represents —COO— or a covalent bond; and h represents 0 or 1;

in the general formula VIII, $R^7$ and $R^8$ independently represent an alkyl group having 1 to 10 carbon atoms or an alkenyl group having 2 to 10 carbon atoms, in either case, any methylene group (—$CH_2$—) may be replaced by an oxygen atom, but in no case may two or more consecutive methylene groups be replaced by oxygen atoms; ring E represents 1,4-cyclohexylene, 1,3-pyrimidine-2,5-diyl, or 1,4-phenylene; ring F represents 1,4-cyclohexylene or 1,4-phenylene; and $Z^5$ represents —C≡C—, —COO—, —$CH_2CH_2$—, or a covalent bond; and in the general formula IX, $R^9$ represents an alkyl group or alkoxy group each having 1 to 10 carbon atoms; $R^{10}$ represents an alkyl group, alkoxy group, or alkoxymethyl group each having 1 to 10 carbon atoms; ring G represents 1,4-cyclohexylene or 1,3-pyrimidine-2,5-diyl; ring I and ring J independently represent 1,4-cyclohexylene or 1,4-phenylene, respectively; $Z^6$ represents —COO—, —$CH_2CH_2$—, or a covalent bond; $Z^7$ represents —C≡C—, —COO—, or a covalent bond; and $Q^7$ represents a hydrogen atom or fluorine atom.

14. A liquid crystal display device composed by using a liquid crystal composition defined in claim 12.

15. A liquid crystal display device composed by using a liquid crystal composition defined in claim 13.

* * * * *